United States Patent [19]

Koden et al.

[11] Patent Number: 5,374,373

[45] Date of Patent: * Dec. 20, 1994

[54] FERROELECTRIC LIQUID CRYSTAL DEVICE

[75] Inventors: Mitsuhiro Koden; Tomoaki Kuratate, both of Nara; Fumiaki Funada, Yamatokoriyama; Kazuhiko Sakaguchi, Toyonaka; Yoshikazu Takehira, Itami; Yutaka Shiomi, Amagasaki; Tohru Kitamura, Kyoto, all of Japan

[73] Assignees: Sharp Kabushiki Kaisha; Daiso Co., Ltd., both of Osaka, Japan

[*] Notice: The portion of the term of this patent subsequent to Sep. 29, 2009 has been disclaimed.

[21] Appl. No.: 58,054

[22] Filed: May 5, 1993

Related U.S. Application Data

[63] Continuation of Ser. No. 493,145, Mar. 13, 1990, abandoned.

[30] Foreign Application Priority Data

Mar. 14, 1989 [JP] Japan ................... 1-62998

[51] Int. Cl.$^5$ .............. C09K 19/34; C09K 19/58; G02F 1/13
[52] U.S. Cl. .................. 252/299.61; 252/299.2; 359/103
[58] Field of Search ............ 252/299.61, 299.2

[56] References Cited

U.S. PATENT DOCUMENTS

| | | | |
|---|---|---|---|
| 4,367,924 | 1/1983 | Clark et al. | 350/350 S X |
| 4,615,586 | 10/1986 | Geary et al. | 350/350 S |
| 4,818,431 | 4/1989 | Eidenschiuk et al. | 252/299.61 |
| 4,909,957 | 3/1990 | Sakaguchi et al. | 252/299.61 |
| 4,973,425 | 11/1990 | Kazuhiko et al. | 252/299.61 |
| 5,026,506 | 6/1991 | Koden et al. | 252/299.61 |
| 5,151,214 | 9/1992 | Koden et al. | 252/299.61 |

FOREIGN PATENT DOCUMENTS

| | | |
|---|---|---|
| 88114609 | 9/1988 | European Pat. Off. |
| 63-30408 | 12/1988 | Japan . |
| 64-9286 | 1/1989 | Japan . |
| 2216540 | 10/1989 | United Kingdom ........... 252/299.61 |

OTHER PUBLICATIONS

Yoshino, K. et al. IEEE Transactions 23 (4) 639, 1988.

*Primary Examiner*—Robert L. Stoll
*Assistant Examiner*—C. Harris
*Attorney, Agent, or Firm*—David G. Conlin; Linda M. Buckley

[57] ABSTRACT

A ferroelectric liquid crystal device having a pair of substrates each provided with voltage application means, an orientation control layer formed on at least one of the substrates, and a layer of ferroelectric liquid crystal composition formed between the pair of substrates, the device being characterized in that the ferroelectric liquid crystal composition comprises at least one compound (a) having an optically active group of the formula (I):

$$-CH \underset{O-C}{\overset{CH_2}{\underset{\|}{\diagup}}} CH- \qquad (I)$$

and at least one compound (b) which is reverse to the compound (a) in the direction of a helical pitch induced in a nematic phase, the liquid crystal composition exhibiting at least a smectic C phase, smectic A phase and nematic phase at least 20 μm in helical pitch.

4 Claims, 1 Drawing Sheet

FERROELECTRIC LIQUID CRYSTAL DEVICE

This is a continuation of copending application(s) Ser. No. 07/493,145 filed on Mar. 13, 1990 now abandoned.

BACKGROUND OF THE INVENTION

1. Field of the Invention

The present invention relates to ferroelectric liquid crystal devices, and more particularly to a ferroelectric liquid crystal device having substrates, voltage application means, an orientation control layer and a ferroelectric liquid crystal layer which comprises a specific ferroelectric liquid crystal composition.

2. Description of the Prior Art

Liquid crystal display devices most widely used presently are those utilizing a nematic phase but having the drawback that they are not adapted for large-capacity display, for example, with 1000×1000 lines. For instance, usual twisted nametic (TN) liquid crystal display devices decrease in contrast with an increase in the number of lines, so that it is practically impossible to fabricate contrasty large-capacity liquid crystal devices of this type with 1000×1000 lines. To overcome the drawback of TN liquid crystal display devices, supertwisted nematic (STN) liquid crystal display devices and double supertwisted namatic (DSTN) liquid crystal display devices have been developed, whereas these devices still have the drawback of decreasing in contrast and in the speed of response with increasing number of lines. Such devices presently available are therefore limited to a display capacity of about 1000×720 lines. On the other hand, the prior art has already provided liquid crystal display devices of the active matrix type wherein thin-film transistors (TFT) are arranged on a substrate. Although it is technically possible to give devices of this type a large display capacity, for example, of 1000×1000 lines, these devices have the drawback of necessitating a long production process and being low in yield and therefore very costly to fabricate.

As promising means for overcoming the foregoing problems, ferroelectric liquid crystal display devices are proposed which operate on a different principle from the TN display device (see N. A. Clark et al., Appl. Phys. Lett., 36, 899(1980)). The proposed device utilizes the chiral smectic C phase, chiral smectic I phase and the like of ferroelectric liquid crystals. The device can be given a great display capacity with an improved speed of response since the memory property of the crystals is utilized. Furthermore, the device can be produced at a low cost since there is no need to use active components such as thin-film transistors. The ferroelectric liquid crystal display device also has the advantage of being wide in field of view. Thus, the device appears very promising as a large-capacity display device having at least 1000×1000 lines.

The liquid crystal material for use in the ferroelectric liquid crystal display device wherein smectic C phase is utilized must of course exhibit the smectic C phase over a wide temperature range around room temperature and needs to fulfill various other requirements. First, the device for large-capacity display must have high-speed responsiveness, and from this viewpoint, the liquid crystal material needs to be highly amendable to spontaneous polarization and low in viscosity. Further the material needs to exhibit satisfactory orientation and bistability when used for the liquid crystal cell. It is also desired that the material be great in tilt angle which is relevant to the contrast and brightness of liquid crystal display.

At present, however, it is impossible for a single compound to fulfill all the desired requirements, so that a plurality of compounds are usually mixed together for use as a liquid crystal composition. To prepare a liquid crystal composition filfulling the requirements for actual use, it is necessary to use numerous single liquid crystal compounds having a wide variety of properties. It is sometimes likely that compounds which per se exhibit no liquid crystal properties will be useful as components of the liquid crystal composition.

SUMMARY OF THE INVENTION

The main object of the present invention which has been accomplished in view of the above situation is to provide a ferroelectric liquid crystal device which is operable in a wide range of temperatures and satisfactory in orientation and memory property and which exhibits high-speed responsiveness at room temperature.

The present invention provides a ferroelectric liquid crystal device having a pair of substrates each provided with voltage application means, an orientation control layer formed on at least one of the substrates, and a layer of ferroelectric liquid crystal composition formed between the pair of substrates, the device being characterized in that the ferroelectric liquid crystal composition comprises at least one compound (a) having an optically active group of the formula (I) given below, and at least one compound (b) which is reverse to the compound (a) in the direction of a helical pitch induced in a nematic phase, the liquid crystal composition exhibiting at least a smectic C phase, smectic A phase and nematic phase at least 20 μm in helical pitch. (Since the chiral smectic C phase and the nonchiral smectic C phase are considered to be thermodynamically identical, these phases will be referred to herein as "smectic C phase" without making distinction therebetween. Similarly, the chiral nematic-phase and the nonchiral nematic phase are considered to be thermodynamically identical, so that these phases will be referred to herein as "nematic phase" without distinguishing therebetween.)

(I)

wherein the asterisked carbon atom is an asymmetic carbon atom.

The optically active groups of the formula (I) are in cis-form and trans-form, which are both usable in the invention. Groups of two forms may be used in mixture.

The compound (a) having an optically active group of the formula (I) are novel compounds. The use of the compounds is one of the features of the present invention.

A preferred group of compounds having an optically active group of the formula (I) are compounds of the formula (II).

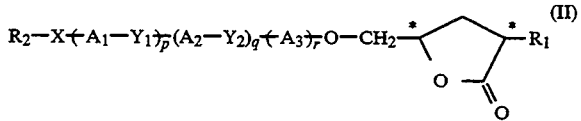

wherein $A_1$, $A_2$ and $A_3$ are each a group containing a 6-membered ring and having or not having a substituent, X is —O—, —COO—, —OCO— or a single bond, $Y_1$ and $Y_2$ are each —COO—, —OCO—, —OCH$_2$—, —CH$_2$O—, —CH$_2$CH$_2$—, —CH=CH—, —C≡C— or a single bond, $R_1$ and $R_2$ are each a straight-chain or branched-chain alkyl having 1 to 15 carbon atoms, p, q and r are each an integer of 0 or 1, and the asterisked carbon atom is an asymmetric carbon atom.

undecyl, 1-methyldecyl, dodecyl, 1-methylundecyl and the like. These alkyl groups may have an asymmetric carbon atom on the carbon chain.

Examples of groups containing a 6-membered ring, having or not having a substituent and represented by $A_1$, $A_2$ or $A_3$ of the formula (II) include benzene ring, pyridine ring, pyrimidine ring, pyrazine ring, pyridazine ring, piperazine ring, cyclohexane ring, dioxacyclohexane ring, bicyclo[2,2,2]octane ring, naphthalene ring and the like. One or more hydrogen atoms in the 6-membered ring-containing groups may be substituted with a fluorine atom, chlorine atom, bromine atom, cyano, nitro, methyl, methoxy or like group.

Examples of preferred compounds represented by the formula (II) are those represented by the following formulae (II)-1 to (II)-7.

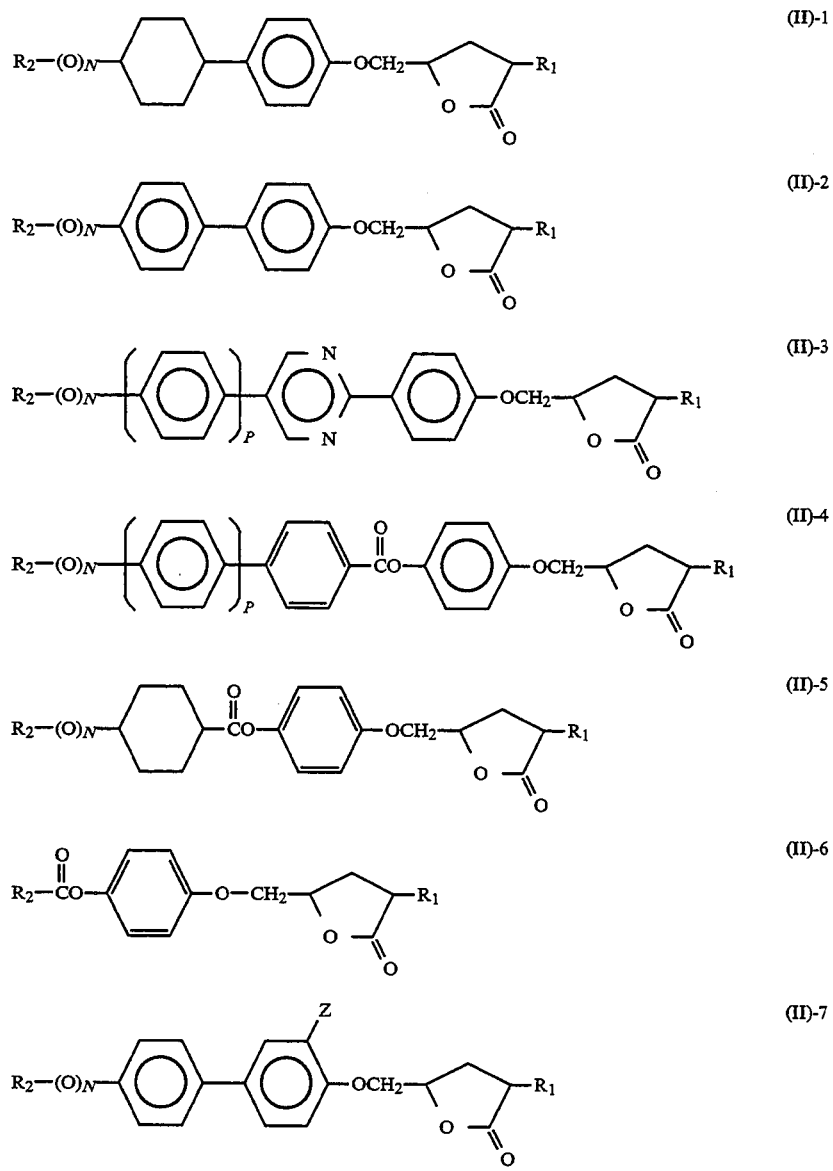

Examples of straight-chain or branched-chain $C_{1-15}$ alkyl groups represented by $R_1$ or $R_2$ of the formula (II) include methyl, ethyl, propyl, isopropyl, butyl, isobutyl, pentyl, 1- or 2-methylbutyl, hexyl, 1- or 3-methylpentyl, heptyl, 1- or 4-methylhexyl, octyl, 1-methylheptyl, nonyl, 1- or 6-methyloctyl, decyl, 1-methylnonyl, wherein $R_1$, $R_2$ and p are each as defined above, n is 0 or 1, and Z is CN or F.

Tables 1 to 7 given later show examples of more preferred compounds represented by these formulae.

Another group of compounds having an optically active group of the formula (I) are those represented by the following formula (II').

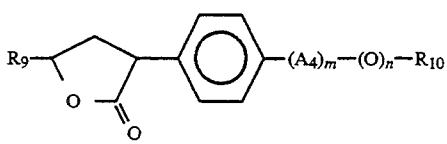

wherein $R_9$ is a straight-chain or branched-chain $C_{1-15}$ aliphatic hydrocarbon group which may have an intervening oxygen atom, $R_{10}$ is a straight-chain or branched-chain $C_{1-15}$ alkyl group, $A_4$ is a phenylene group or cyclohexane group, and m and n are each 0 or 1.

Examples of straight-chain or branched-chain $C_{1-15}$ aliphatic hydrocarbon groups which may have an intervening oxygen atom include alkyl, alkoxyalkyl and alkenyloxyalkyl groups. These groups may be 1 to 15 in the total number of carbon atoms and straight-chain or branched-chain groups. Specific examples of alkyl groups are those exemplified for $R_1$ and $R_2$. Specific examples of alkoxyalkyl groups are methoxymethyl, ethoxymethyl, propoxymethyl, pentyloxymethyl, hexyloxymethyl and like groups. Specific examples of alkenyloxyalkyl groups are allyloxymethyl, allyloxyethyl and like groups.

Table 8 shows examples of more preferred compounds of the formula (II').

The optically active compound of the formula (II), for example, the compound wherein $A_1=$

$A_2=$

X=single bond, $Y_1$=single bond, $Y_2$=single bond, p=1, q=1, and r=0 can be prepared by reacting optically active epichlorohydrin with a phenol in the presence of a base to obtain a compound of the formula (VI)

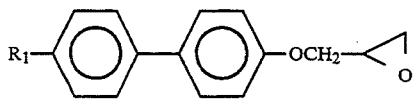

and reacting this compound with a malonic acid ester of the formula (VII)

$$R_2-CH(COOR_6)_2 \quad (VII)$$

in the presence of a base. In the above formulae, $R_1$ and $R_2$ are each as defined for the formula (I), and $R_6$ is methyl, ethyl or like lower alkyl group.

A typical method for preparing the optically active compound of the formula (II') will be illustrated in the following Preparation.

The optically active compounds of the formulae (II) (inclusive of (II)-1 to (II)-7 and (II')) do not always exhibit a liquid crystal phase. Even when exhibiting this phase, such compounds are not always useful in respect of the phase series and the temperature range of the smectic C phase. Accordingly, it is much more desirable to use these compounds in combination with other compounds than to use them singly.

When the compound of the formula (II) or (II') is added in a suitable amount to nonchiral smectic liquid crystal compounds or composition or to chiral smectic liquid crystal compounds or composition, the composition undergoes enhanced spontaneous polarization to exhibit high-speed responsiveness as a ferroelectric liquid crystal composition. However, if the compound is added in a large amount, the use of the composition is very likely to encounter problems such as the crystallization of the added compound in the composition and a reduction in the temperature of transition from $S_C$ to $S_A$. It is therefore desirable to add the compound in an amount of 0.1 to 20%, more preferably about 0.5 to 10%.

The compounds to be used in combination with compounds of the formulae (II) and (II') are those represented by the following formulae (VIII) to (X).

$$R_7-Z_1-B_1-D_1-B_2-Z_2-R_8 \quad (VIII)$$

$$R_7-Z_1-B_1-D_1-B_2-D_2-B_3-Z_2-R_8 \quad (IX)$$

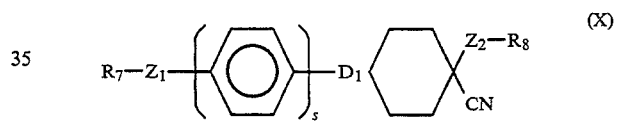

wherein $B_1$, $B_2$ and $B_3$ are each independently a benzene ring, cyclohexane ring, bicyclo[2,2,2]octane ring, pyridine ring, pyrimidine ring, pyrazine ring, pyridazine ring, piperazine ring, dioxacyclohexane ring, naphthalene ring or like group containing a 6-membered ring, the hydrogen atom of which may be substituted with a fluorine atom, chlorine atom, bromine atom, cyano, nitro, methyl, methoxy or like group, $D_1$ and $D_2$ are each a single bond or —COO—, —OCO—, —CH= CH—, —C≡C—, —CH=CH—COO—, —O-CO—CH=CH—, —CH$_2$CH$_2$—, —OCH$_2$—, —CH- 2O—, —COS— or —SCO— group, $Z_1$ and $Z_2$ are each a single bond or —COO—, —OCO—, —O—, —S—, —OCOO— or —CO— group, $R_7$ and $R_8$ are each independently a straight-chain or branched-chain alkyl group having 1 to 15 carbon atoms and containing or not containing an asymmetric carbon atom, and s is an integer of 1 or 2.

In the case where a ferroelectric liquid crystal composition is to be prepared from compounds of the formulae (II) and (II'), various properties or characteristics of the composition need to be considered collectively so that when the composition is used for a ferroelectric liquid crystal device, the device will exhibit satisfactory characteristics. According to the invention, the ferroelectric liquid crystal composition is so prepared as to exhibit at least a smectic C phase, smectic A phase and nematic phase having a helical pitch of not smaller than 20 μm in order that the ferroelectric liquid crystal device to be obtained is satisfactory not only in liquid crystal temperature range, tilt angle and response characteristics but also in orientation and memory property. When the composition exhibiting such a phase series is fabricated into a ferroelectric liquid crystal device and thereafter cooled from an isotropic liquid state, a uniform orientation is readily obtained first in the nematic phase since the helical pitch in this phase is at least 20 μm and is therefore sufficiently greater than the cell thickness (usually about 1.5 to about 8 μm) of the device. If the uniform orientation is obtained in the nematic phase, a uniform orientation is easily obtained in the smectic A phase when the device is further cooled. A satisfactory orientation is obtained also in the smectic C phase when the device is further cooled. When thus satisfactory in orientation, the device is also satisfactory in memory property.

The ferroelectric liquid crystal composition exhibiting such smectic C phase, smectic A phase and namatic phase having a helical pitch of at least 20 μm can be obtained by using an optically active compound which is reverse to the optically active compounds of the formulae (II) and (II') in the direction of the helical pitch to be induced in the nematic phase, in combination with the compound having an optically active group of the formula (I) or with the optically active compound of the formula (II) in a suitable ratio. The combination can be determined, for example, through trial and error so that the helical pitch of the nematic phase will be at least 20 μm, and various other methods.

An exemplary method will be described next. A linear addition rule represented by the equation (XI) is known as to the pitch of the nematic phase (see J. E. Adams and W. E. L. Hass, Mol. Cryst. Liq. Cryst., 16, 33(1972)).

$$1/P = \Sigma(C_i/P_i) \quad (XI)$$

wherein $\Sigma C_i = 1$, P is the pitch of a liquid crystal mixture, and $C_i$ is the weight concentration of each component having an intrinsic pitch $P_i$.

First, various optically active compounds are added to a liquid crystal compound or composition exhibiting a nematic phase, followed by the measurement of the nematic phase to estimate the intrinsic pitch $P_i$ of each component. Next, the concentrations of the respective components are adjusted so that the pitch of nematic phase of the ferroelectric liquid crystal composition to be obtained becomes not smaller than 20 μm, using the values obtained.

The optically active compounds to be used for the adjustment of pitch can be those of the compounds represented by the formulae (VIII), (IX) and (X) wherein one or each of $R_7$ and $R_8$ is an optically active group. If possible, such compounds to be used are preferably those identical with the compound having an optically active group of the formula (I), i.e., the optically active compound of the formula (II) or (II)' in the direction of spontaneous polarization to be induced in the smectic phase and having a great value thereof, because it is said that the greater the value of spontaneous polarization grows, the higher the speed of response generally.

From such a viewpoint, the compounds having an optically active group of the formula (III) can be mentioned as examples of compounds which are identical with the optically active compounds of the formulae (II) and (II') in the direction of spontaneous polarization to be induced in the smectic C phase, have a relatively great value of spontaneous polarization and reverse to these compounds in the direction of helical pitch to be induced in the nematic phase.

wherein Z is —COO—, —OCO—, —O— or —CO—, $R_3$ is a straight-chain or branched-chain alkyl group having 1 to 15 carbon atoms, B is $CH_3$, CN, $CF_3$, $CHF_2$, $CH_2F$ or a halogen atom (Cl, Br or F), and the asterisked carbon atom is an asymmetric carbon atom. Preferred examples of such compounds are those given below, whereas the compounds to be used in the invention are not limited to these examples.

1) Compounds of the formula (XI):

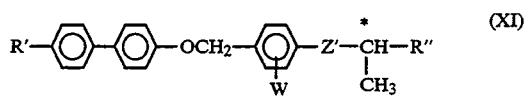

For example, R' is $C_{10}H_{21}O$, R" is $C_6H_{13}$ and W is H, Z' is COO (see K. Terashima et al., Mol. Cryst. Liq. Cryst., 141, 237(1986)).

2) Compounds of the formula (XII):

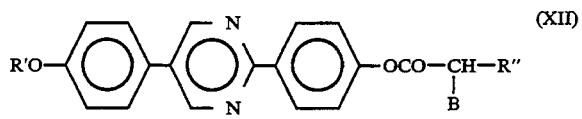

For example, B is F (see J. Börneburg et al., 12th Int. LC Conf. FF-18(1988)).

3) Compounds of the formula (XIII):

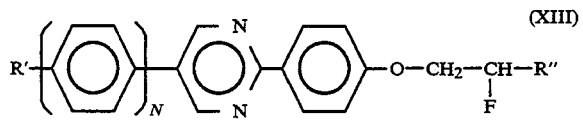

For example, R' is $C_6H_{13}$, $C_7H_{15}$, $C_8H_{17}$ or $C_9H_{19}$, R" is $C_5H_{11}$, $C_6H_{13}$, $C_7H_{15}$, $C_9H_{19}$ or $C_{10}H_{21}$, and n is 0 or 1 (see Nohira et al., Papers Presented at 14th LC Conf., 40(1988)).

4) Compounds of the formula (XIV):

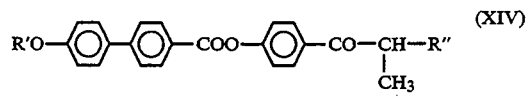

For example, R' is $C_8H_{17}$, and R" is $C_6H_{13}$ (see A. Yoshizawa et al., Jpn. J. Appl. Phys., 28, L1269 (1989)).

5) Compounds of the formula (XV):

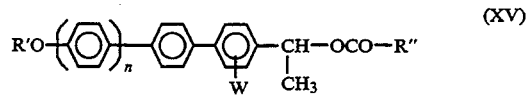

n is 0 or 1, W is H, Cl, Br, F or CN (see Yoshida et al., 15th LC Conf., 1AO1(1989)).

6) Compounds of the formula (XVI):

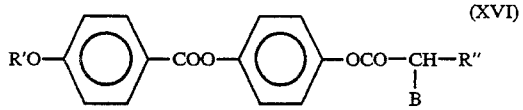  (XVI)

For example, R' is $C_8H_{17}$, R'' is

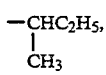

and B is Cl (see T. Sakurai et al., J. Chem. Soc., Commun. 978 (1986)).

7) Compounds of the formula (XVII):

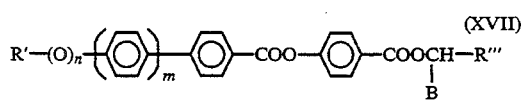  (XVII)

For example, m is 0 or 1, , R'—(O)$_n$— (n is 0 or 1) is $C_7H_{15}O$—, $C_8H_{17}O$— or $C_{10}H_{21}$—, B is $CH_3$, $CF_3$, $CHF_2$ or $CH_2F$, and R''' is $C_6H_{13}$, $C_8H_{17}$ or $CH_2COOC_2H_5$ (see, for example, K. Yoshino et al., Jpn. J. Appl. Phys., 26, L77(1987)).

8) Compounds of the formula (XVIII):

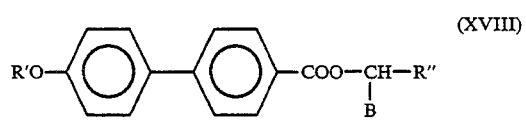  (XVIII)

For example, R' is $C_9H_{19}$, R'' is —CH(CH$_3$)$_2$, and B is $CH_3$ or CN (see I. Sage et al., Ferroelectrics, 85 (1988)).

9) Compounds of the formula (XIX):

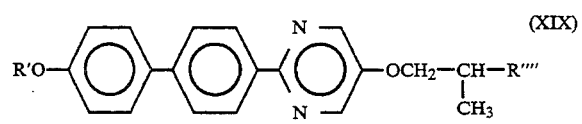  (XIX)

For example, R' is $C_6H_{13}$, and R'''' is

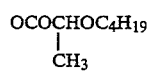

(see Miyazawa et al., Papers Presented at 14th LC Conf., 52(1988)).

10) Compounds of the formula (XX):

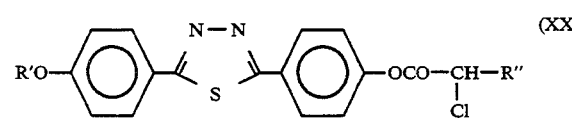  (XX)

For example, R' is C H, and R'' is $CH_2CH(CH_3)_2$ (see C. Tschierske et al., 2nd Ind. Conf. FLC, 83 (1989)).

11) Compounds of the formula (XXI):

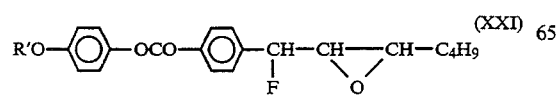  (XXI)

For example, R' is $C_{10}H_{21}$ (see D. M. Walba et al., J. Am. CHem. Soc., 110, 8686(1988)).

12) Compounds of the formula (XXII):

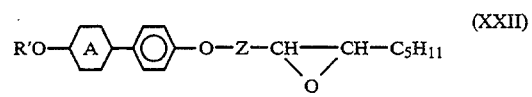  (XXII)

For example, R' is $C_8H_{17}$,

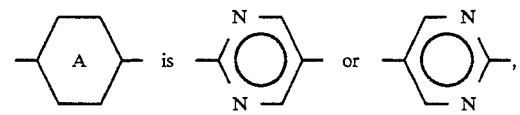

and Z is CO or $CH_2$ (see Murakami et al., Papers Presented at 14th LC Conf., 20(1988), and Murakami et al., 15th LC Conf., 1A16(1988)).

13) Compounds of the formula (XXIII):

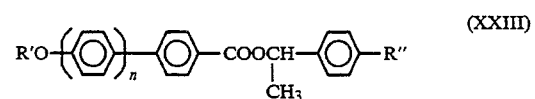  (XXIII)

For example, R' is $C_8H_{17}$, and R'' is $C_8H_{17}$ (see M. Koden et al., Mol. Cryst. Liq. Cryst. Lett., 6, 197(1989)).

14) Compounds of the formula (XXIV):

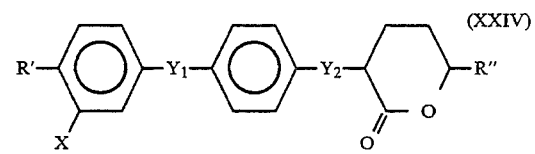  (XXIV)

R' is $C_{10}H_{21}$, R'' is $C_6{13}$, and Y' is —COO—, —OEO or —OCH$_2$, $Y_2$ is COO or O, X is H or Cl (see N. Nakauchi et al., Jpn. J. Appl. Phys. 28, L1258(1989), and Ikemoto et al., 15th LC Conf., 1A05 (1989)).

15) Compounds of the formula (XXV):

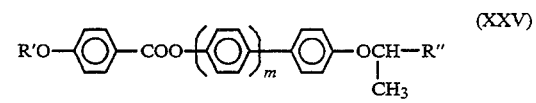  (XXV)

For example, R' is $C_8H_{17}$, R'' is $C_4H_9$ or $C_6H_{13}$, and m is 0 or 1.

16) Compounds of the formula (XXVI):

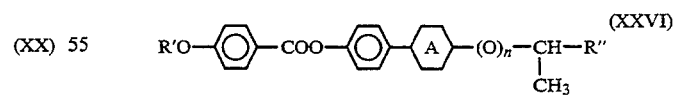  (XXVI)

For example, R' is $C_8H_{17}$, R'' is $C_2H_5$ or $C_3H_7$, n is 0 or 1, and

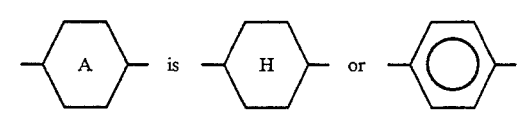

In the foregoing formulae (XI) to (XXVI), R' and R'' are the same or different and are each a straight-chain or branched-chain $C_{1-15}$ alkyl or alkoxy group, preferably $C_{5-11}$ alkyl or alkoxy group, R''' is a straight-chain or branched-chain $C_{1-15}$ alkyl or alkoxy group or $CH_2COOC_2H_5$, R'''' is

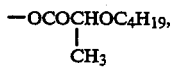

and B is $CH_3$, $CF_3$, $CHF_2$, $CH_2F$, halogen (Cl, F or Br) or CN, W is H, halogen or CN, Z' is O or COO.

Next, the ferroelectric liquid crystal device embodying the invention will be described.

Figure 1:
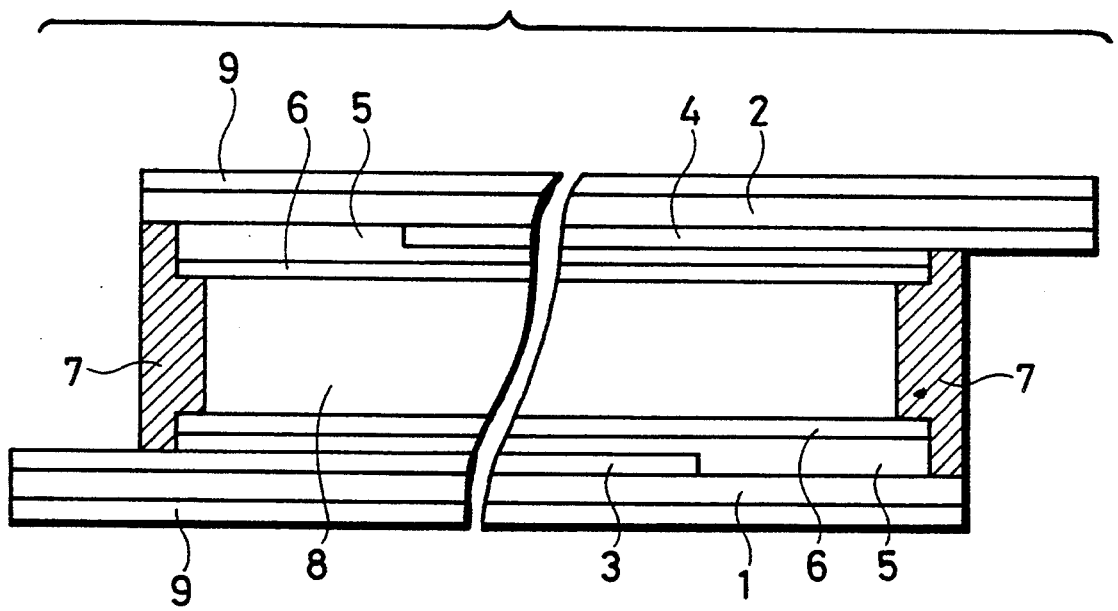
FIG. 1 is a sectional view showing an example of a liquid crystal device of the transmitting type, wherein the ferroelectric liquid crystal of the present invention is used.

FIG. 1 is a sectional view showing an example of liquid crystal device wherein the ferroelectric liquid crystal composition of the invention is used.

The example shown in FIG. 1 is a display device of the transmitting type which comprises insulating substrates 1 and 2, electrically conductive films 3 and 4, insulating films 5, orientation control layers 6, a sealant 7, the ferroelectric liquid crystal composition 8, and a polarizing plate 9.

The insulating substrates 1 and 2 are light-transmitting substrates, which are usual glass substrates. The substrates 1 and 2 are respectively formed with transparent electrodes 3 and 4 of specified pattern, each in the form of a conductive film of $InO_3$, $SnO_2$, ITO (Indium-Tin Oxide) or the like.

The insulating film 5 is usually formed over the electrode but can be dispensed with as the case may be. Usable as the insulating film 5 is, for example, an inorganic thin film of $SiO_2$, $SiN_x$, $Al_2O_3$, or an organic thin film of polyimide, photoresist resin, high polymer liquid crystal or the like. The insulating film 5, when in the form of an inorganic thin film, can be formed by sputtering, CVD (Chemical Vapor Deposition), solution coating or like method. Further the insulating film 5, when in the form of an organic thin film, can be prepared by applying a solution of an organic substance or of a precursor thereof by spinner coating, dip coating, screen printing, roll coating or like method, and curing the coating under predetermined conditions (as by heating or irradiation with light), or by vacuum evaporation, sputtering, CVD or LB (Langumuir-Blodgett) method.

The orientation control layer 6 is formed over the insulating film 5. However, if the insulating film 5 is omitted, the orientation control layer 5 is formed directly over each of the conductive layers 3 and 4. The orientation control layer is in the form of an inorganic layer or an organic layer.

The orientation control layer, when of the in-organic type, is usually formed by vacuum evaporation of silicon oxide. Rodary vacuum evaporation or like method can also be resorted to. When the orientation control layer is of the organic type, nylon, polyvinyl alcohol, polyimide or the like is usable, and the surface of the layer is usually rubbed. Further orientation can be effected with use of a high polymer liquid crystal or LB film or a magnetic field, or by spacer edge method. The layer can also be prepared from $SiO_2$, $SiN_x$ or the like by vacuum evaporation, sputtering or CVD, followed by rubbing of the surface.

Subsequently, the two insulating substrates are placed over each other, and the liquid crystal composition 8 is injected into the space therebetween to obtain a ferroelectric liquid crystal device.

Figure 2:
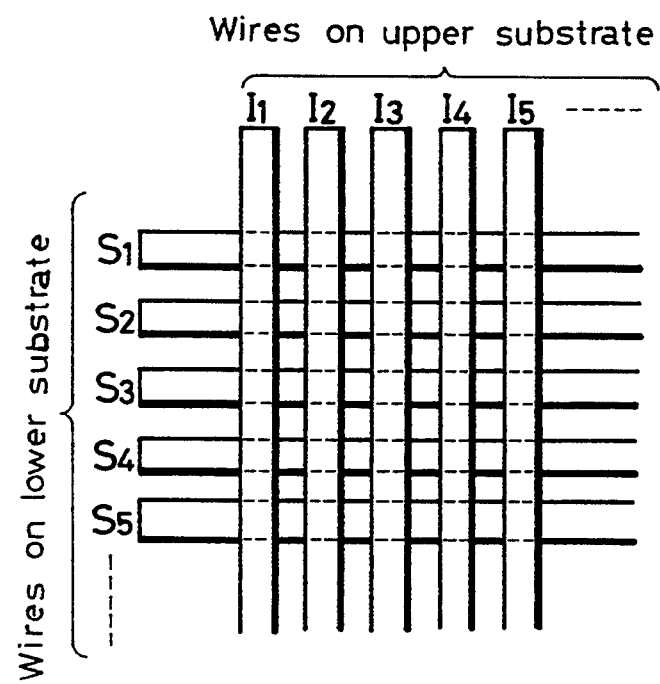
FIG. 2 is a schematic plan view of a display device having a large capacity matrix, wherein the wires on upper and lower substrates are combined into a matrix as shown.

Although the device described with reference to FIG. 1 is a switching device with one pixel, the ferroelectric liquid crystal composition of the invention can be used for display devices with a large-capacity matrix. In this case, the wires on upper and lower substrates are combined into a matrix as shown in the schematic plan view of FIG. 2. The liquid crystal device of the matrix type can be driven by various drive methods heretofore proposed (see, for example, Wakita, Uemura, Ohnishi, Ohba, Furubayashi and Ohta, National Technical Reports 33, 44(1987)).

Synthesis of compounds of the formula (I)
Preparation 1

(i) To a mixture of 5.55 g of R-(−)-epichlorohydrin (optical purity: 99% or more), 2.46 g of 4-(trans-4-n-pentylcyclo-hexyl) phenol of the formula:

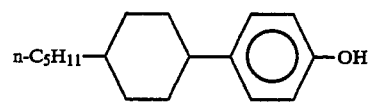

and 0.04 g of benzyltriethylammonium chloride was dropwise added a solution of 0.45 g of sodium hydroxide in 15 ml of water taking 20 minutes at 60° C. under stirring. The reaction mixture was refluxed for an hour and then cooled to room temperature. Further the mixture was extracted twice with ether and washed once with a saturated aqueous solution of sodium chloride. The solvent was epoxypropyl 4-(trans-4-n-pentylcyclohexyl)phenyl ether (1.8 g) of the formula.

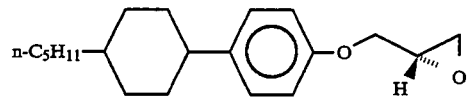

$[\alpha]_D^{25}$: +4.44° (C=1.36, $CH_2Cl_2$)
NMR($CDCl_3$) δ: 0.45–2.50(21H,m), 2.50–3.00 (2H,m), 3.15–3.50 (1H,m), 3.70–4.30 (2H,m), 6.79 (2H,d,J=9.0 Hz), 7.09 (2H,d,J=9.0 Hz)

(ii) A 50% by weight suspension of sodium hydride in mineral oil (222 mg) was washed twice with dry ether, to which 10 ml of dry tetrahydrofuran was added. To the suspension was dropwise added 1.07 g of dimethyl n-butylmalonate taking 5 minutes at 40° C. under stirring. To the resultant was dropwise added 1.41 g of (S)-2,3-epoxypropyl-4-(trans-4-n-pentylcyclohexyl) phenyl ether obtained in the above (i). The reaction mixture was refluxed for 20 hours under stirring and then cooled to room temperature. 4N-Hydrochloric acid was dropwise added to the reaction mixture to adjust it to pH1. The resultant was extracted twice with ether and washed once with saturated sodium chloride aqueous solution, and the solvent was evaporated under reduced pressure. The residue was purified by a silica gel column chromatography to obtain two γ-lactone derivatives, i.e., a (2S,4S) isomer of the following formula (500 mg) and the corresponding (2R,4S) isomer (440 mg).

[Compound No. 110, (2S, 4S)isomer]

The properties of the (2S,4S)isomer are as follows:

Phase transition temperature: C $\xrightarrow{84°\ C.}$ I $[\alpha]_D^{23}$: +33.45° (C=0.658, $CH_2Cl_2$)
NMR($CDCl_3$) δ: 0.88–1.98(30H,m), 2.38–2.67(3H,m), 4.07–4.13(2H,m), 4.67–4.73(1H,m), 6.83(2H,d,J=8.3 Hz), 7.12(2H,d,J=8.3 Hz) IR: νmax(KBr): 1762 $cm^{-1}$
Elementary analysis for $C_{26}H_{40}O_3$ Calculated (%): C:77.95; H:10.07 Found (%): C:77.91; H:10.12

Preparation 2

(i) 2.50 g of a phenol derivative of the formula:

4.25 g of R-(—)-epichlorohydrin and 20 mg of benzyl triethyl ammonium chloride (the latter two compounds were the same ones as used in Preparation 1) were dissolved in 3 ml of dimethylformamide. To the solution was dropwise added 24% by weight sodium hydroxide aqueous solution (1.2 equivalents) at 60° C. The mixture was allowed to react for 40 minutes at the same temperature, then cooled to room temperature and extracted with ether. The solvent was evaporated under reduced pressure. The residue was purified by a silica gel column chromatography to obtain an S isomer of glycidyl ether (1.62 g) of the following formula:

mp: 90° C.
$[\alpha]_D^{25}$: +4.44° (C=1.01, $CH_2Cl_2$)
NMR($CDCl_3$) δ: 0.50–3.00(19H,m), 3.10–3.50(1H,m), 3.80–4.30(2H,m), 6.75–7.60(8H,m)

(ii) 370 mg of the S-isomer of glycidyl ether obtained in the preceding process (i), 442 mg of diethyl n-propylmalonate, 134 mg of potassium tert-butoxide and 3 ml of tert-butyl alcohol were mixed and refluxed for 10 hours under stirring. The reaction mixture was allowed to cool to room temperature. After 4N-hydrochloric acid was added to the mixture to adjust it to pH1, the mixture was washed with water and methanol to give white crystals. The crystals were purified by a silica gel chromatography to give 240 mg of a (2S,4S) isomer of the following formula and 140 mg of the corresponding (2R,4S)isomer.

[Compound No. 210, (2S,4S)isomer]

The properties of the (2S,4S)isomer are as follows.

Phase transition temperature: C $\xrightarrow{115°\ C.}$ I $[\alpha]_D^{25}$: +32.67° (C=1.081, $CH_2Cl_2$)
NMR($CDCl_3$) δ: 0.70–3.00(27H,m), 4.00–4.25(2H,m), 4.40–4.85(1H,m), 6.60–7.60(8H,m) IR νmax(KBr): 1762 $cm^{-1}$ (C=O)

Preparations 3 to 5

The (2S,4S)isomers of γ-lactone derivatives of the following formulas were obtained in the same manner as that in Preparation 2.

[Compound No. 202, (2S,4S)isomer]

[Compound No. 204, (2S,4S)isomer]

[Compound No. 208, (2S,4S)isomer]

Preparation 6

(i) 1.01 g of the compound of the formula:

2.01 g of R-(—)-epichlorohydrin and 16 mg of benzyl triethyl ammonium chloride (the latter two compounds were the same ones as used in Preparation 1) were mixed and heated to 70° C. To the mixture was dropwise added 650 mg of 24% by weight sodium hydroxide aqueous solution. The resultant was stirred for 2 hours at 70° C., and cooled to room temperature. The mixture was extracted trice with chloroform, dried over anhydrous magnesium sulfate and distilled under reduced pressure to remove the solvent. The residue was recrystallized from hexane to obtain 380 mg of an S isomer of glycidyl ether of the following formula:

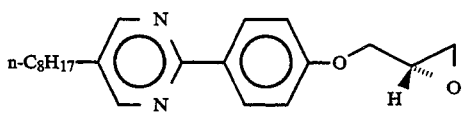

mp: 65° C.

[α]$_D^{25}$: +1.90° (C=0.46, CH$_2$Cl$_2$)

NMR(CDCl$_3$) δ: 0.6–3.0(19H,m), 3.2–3.6(1H,m), 3.9–4.5(2H,m), 6.99(2H,d,J=9.0 Hz), 8.36(2H,d,J=9.0 Hz), 8.55(2H,s)

(ii) 320 mg of the S-isomer of glycidyl ether obtained in the preceding process (i), 400 mg of dimethyl n-hexylmalonate and 116 mg of potassium tert-butoxide were dissolved in 3.5 ml tert-butyl alcohol, followed by refluxing under stirring for 6 hours. The reaction mixture was treated in the same manner as that in Preparation 2 to obtain 270 mg of a mixture of diastereomers of a γ-lactone derivative [(2S,4S)/(2R,4S)=9/1]. Further, the mixture was purified to obtain 210 mg of the (2S,4S)isomer of the -lactone derivative of the following formula:

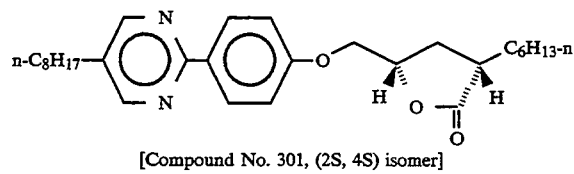

[Compound No. 301, (2S, 4S) isomer]

NMR(CDCl$_3$) δ: 0.85–0.90(6H,m), 1.27–1.64(21H,m), 1.82–1.95(2H,m) 2.47–2.70(4H,m), 4.13–4.25(2H,m), 4.70–4.77(1H,m), 6.99(2H,d,J=9.1 Hz), 8.37(2H,d,J=8.9 Hz), 8.57(2H,s) IR(nujol): 1778 cm$^{-1}$ The compounds of the formula (I) which were obtained in the above Preparations 1 to 6 and have an optically active group were used as Compounds No. 110, No. 210, No. 202, No. 204, No. 208 and No. 301 in the following examples.

Preparation 7

(i) To a suspension of 2.82 g of 4-(4-n-octylphenyl)phenol in 40 ml of 1,2-dichloroethane were added under ice cooling, 6 ml of a solution of boron trichloride (2M) in 1,2-dichloroethane, and then 0.82 ml of methyl thiocyanate and 1.33 g of aluminum chloride. The mixture was stirred at room temperature until the aluminum chloride is dissolved, further stirred for 3 hours at 80° C. and cooled to room temperature. To the resulting mixture was added further 33 ml of 4N-sodium hydroxide solution. The mixture was stirred for 30 minutes at 75° to 80° C. After cooling, the reaction mixture was washed with methylene chloride. The aqueous phase was adjusted to pH2 with 6N hydrochloric acid and extracted with ether. The extract was dried and evaporated under reduced pressure to obtain crude crystals. The crystals were purified by a silica gel column chromatography to give 2.03 g of 4-(4-n-octylphenyl)-2-cyanophenol.

(ii) To a solution of 1.9 g of 4-(4-octylphenyl)-2-cyanophenol obtained in the preceding (i) in 40 ml of tert-butyl alcohol were added 832 mg of potassium tert-butoxide, and then 2.5 ml of R-(−)-epichlorohydrin and 100 mg of 4-(N,N-dimethylamino)pyridine. The resultant was stirred for 2 days at room temperature arid concentrated under reduced pressure. The residue to which water was added was extracted with ether. The extract was dried and distilled to obtain a crude product. The product was purified by a silica column chromatography to give 750 mg of an S-isomer of glycidyl ether of the following formula.

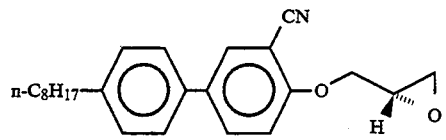

(iii) A mixture of 363 mg of the S-isomer of glycidyl ether obtained in the preceding (ii), 303 mg of diethyl n-propylmalonate, 157 mg of potassium tert-butoxide and 10 ml of tert-butyl alcohol was refluxed under stirring for 6 hours. The reaction mixture was allowed to cool to room temperature, adjusted to pH2 by adding water and then 4N-hydrochloric acid, and extracted with chloroform. An oil obtained from the extract was subjected to a silica gel column chromatography to afford 33 mg of a (2S,4S)isomer and 25 mg of (2R,4S)isomer of the lactone derivative of the following formulae.

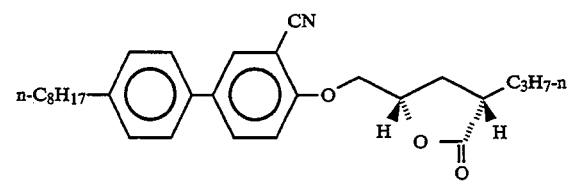

[Compound No. 502, (2S, 4S) isomer]

Phase transition temperature: C $\xrightarrow{86° C.}$ I

[α]$^{23}$: +31.83° (C=1.09, CH$_2$Cl$_2$)

NMR(CDCl$_3$) δ: 0.88(3H,t,J=6.6 Hz), 0.97(3H,t,J=7.1 Hz), 1.25–1.32 (10H,m), 1.41–1.58(3H,m), 1.59–1.66(2H,m), 1.85–2.07(2H,m), 2.55–2.78(4H,m), 4.31(2H,d,J=4.3 Hz), 4.74–4.83(1H,m), 7.00–7.77(7H,m) IR (KBr): 2232 cm$^{-1}$ (C≡N) 1768 cm$^{-1}$ (C=0)

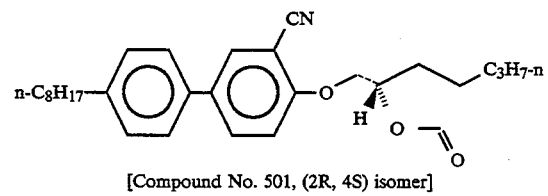

[Compound No. 501, (2R, 4S) isomer]

Phase transition temperature: C $\xrightarrow{80° C.}$ I

[α]$_D^{23}$: +18.26° (C=0.87, CH$_2$Cl$_2$)

NMR(CDCl$_3$) δ: 0.88(3H,t,J=6.8 Hz), 0.98(3H,t,J=7.1 Hz), 1.25–1.27(12H,m), 1.45–1.56(2H,m), 1.60–1.62(1H,m), 1.85–1.95(1H,m), 2.12–2.22(3H,m), 3.05–3.10(1H,m), 4.19(1H,dd,J=3.3 Hz, 10.3 Hz), 4.37(1H,dd,J=3.3 Hz, 10.3 Hz), 4.84–4.89(1H,m), 7.00–7.77(7H,m) IR (KBr): 2232 cm$^{-1}$ (νC≡N) 1768 cm$^{-1}$ (νC=0)

Preparation 8

(i) 25 g of 4-Iodophenol was dissolved in 100 ml of tert-butyl alcohol. To the solution was added 14.01 g of potassium tert-butoxide, and the resultant was stirred for 4 hours at 40° to 45° C. To the solution was gradually added n-octylbromide (24.14 g) under ice cooling and further the mixture was stirred for 3 hours room temperature. The solvent was evaporated from the reaction mixture under reduced pressure. The residue to which water was added was extracted with chloroform to obtain a crude product, which was subjected to a silica gel column chromatography. The solvent was evaporated under reduced pressure from the eluate obtained by use of chloroform as an eluent to give 12 g of the intended compound of 4-(n-octyloxy) iodobenzene.

(ii) A mixture of 25 g of 4-bromo-2-fluorophenol, 19 g of potassium carbonate and 100 ml of acetone was refluxed under stirring for 30 minutes. The reaction mixture was cooled, to which 17.40 g of benzyl chloride were dropwise added taking 15 minutes. The resultant was refluxed under stirring for 7 hours and filtered. The filtrate was distilled to remove acetone. The residue to which water was added was extracted with chloroform. The extract was washed, dried and purified by a silica gel column chromatography using chloroform. The eluate was evaporated under reduced pressure to obtain 22.24 g of the intended benzyl 4-bromo-2-fluorophenyl ether.

(iii) Benzyl 4-(4'-n-octyloxyphenyl)-2-fluorophenyl ether (5.6 g) was prepared from 14.06 g of benzyl 4-bromo-2-fluorophenyl ether obtained in the above (ii), 1.22 g of ribbon-like magnesium and 11.61 g of 4-n-octyloxyiodobenzene.

(iv) 4-(4'-n-Octyloxyphenyl)-2-fluorophenol (3.71 g) was prepared from a mixture of 5 g of benzyl 4-(4'-n-octylphenyl)-2-fluorophenyl ether obtained in the above (ii), 2.5 g of 5% Pd-C (water content: 52%) and 200 ml of ethyl acetate.

(v) S-Isomer of glycidyl ether of the following formula (2.17 g) was prepared from 2.68 g of 4-(4'-n-octyloxyphenyl)-2-fluorophenol obtained in the above (iv), 1.12 g of potassium tert-butoxide, 3.3 ml of R-(−)-epichlorohydrin, 50 mg of 4-(N,N-dimethylamino)pyridine and 60 ml of tert-butyl alcohol.

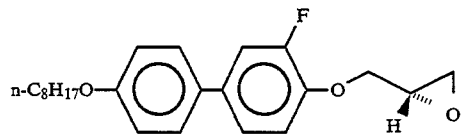

(vi) A mixture of 650 mg of the S-isomer of glycidyl ether obtained in the above (v), 529 mg of diethyl n-propylmalonate, 274 mg of potassium tert-butoxide and 20 ml of tert-butyl alcohol was refluxed under stirring for 1.5 hours. The resultant was treated in the same manner as in Preparation 1 to obtain 310 mg of a (2S,4S)isomer and 102 mg of a (2R,4S)isomer of a γ-lactone derivative of the following formula.

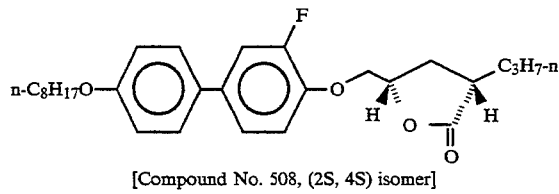

[Compound No. 508, (2S, 4S) isomer]

Phase transition temperature: C $\xrightarrow{125° \text{C.}}$ I $[\alpha]_D^{21}$: +38.35° (C=1.02, CH$_2$Cl$_2$)
NMR(CDCl$_3$) δ: 0.89(3H,t,J=6.7 Hz), 0.97(3H,t,J=7.1 Hz), 1.2–1.6(13H,m), 1.74–2.0(4H,m), 2.45–2.6(1H,m), 2.6–2.75(1H,m), 3.99(2H,t,J=6.6 Hz), 4.15–4.3(2H,m), 4.7–4.8(1H,m), 6.8–7.5(7H,m) IR (KBr): 1764cm$^{-1}$ (νC=O) MS (EI): m/z 456(M+)

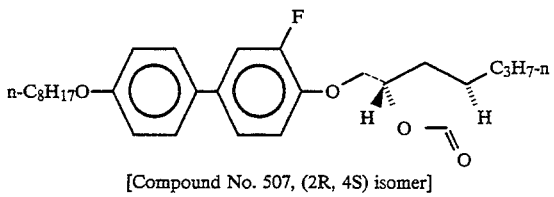

[Compound No. 507, (2R, 4S) isomer]

Phase transition temperature: C $\xrightarrow{100° \text{C.}}$ I $[\alpha]_D^{21}$: +21.51° (C=0.79,CH$_2$Cl$_2$)
NMR(CDCl$_3$) δ: 0.89(3H,t,J=6.8 Hz), 0.98(3H,t,J=7.1 Hz), 1.2–1.55(13H,m), 1.75–1.9(3H,m), 2.05–2.2(1H,m), 2.45–2.56(1H,m), 2.85–2.95(1H,m), 3.99(2H,t,J=6.6 Hz), 4.15(1H,dd,J=3.5, 10.3 Hz), 4.26(1H,dd,J=3.5, 10.3 Hz), 4.75–4.85(1H,m), 6.9–7.4(7H,m) IR (KBr): 1770 cm$^{-1}$ (νC=O) MS (EI): m/z 456(M+)

Synthesis of compounds of the formula (II')

Preparation 9

(i) To a mixture of 50% sodium hydroxide (40 g), (S)-epichlorohydrin (24 g) and tetrabutyl ammonium hydrogen sulfate (400 mg) is added dropwise n-hexanol (6 ml) while cooling at 20°–25° C. After stirring the reaction mixture at the same temperature for additional 3 hours, water is added to the mixture and the product is extracted with ether. The extract is purified by distillation under reduced pressure to give (S)-n-hexylglycidyl ether (3.35 g).

(ii) To a solution of diisopropylamine (505 mg) in tetrahydrofuran (10 ml) cooled at −78° C. is added drop-wise a 15% solution of n-butyllithium in hexane (3 ml) and the temperature is raised gradually to 0° C. and the mixture is stirred for 30 minutes. To this reaction solution is added dropwise a solution of 4-(4'-n-heptyl)-biphenylacetic acid (682 mg) in tetrahydrofuran (3 ml) and the mixture is stirred for 1 hour. The reaction solution is cooled to −78° C. and a solution of (S)-n-hexylglycidyl ether (445 mg) in tetrahydrofuran (1 ml) is added dropwise. After the temperature of the reaction solution is gradually raised to room temperature and the reaction solution is stirred for 6 hours, water is added and the mixture is acidified with hydrochloric acid, followed by extraction of the product with chloroform. To the extract is added dry benzene and a catalytic amount of sulfuric acid and the mixture is stirred with heating for 6 hours while draining benzene in portions. After cooling, the benzene is distilled off under reduced pressure and the residue is purified by silica gel column chromatography to give γ-lactone derivatives (2S,4R) (401 mg) and (2R,4R) (465 mg) of the following formulas, respectively.

(2S,4R) isomer:

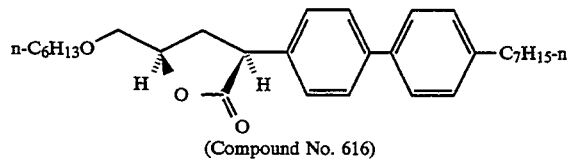

(Compound No. 616)

Phase transition temperature: C —71° C.→ I $[\alpha]_D^{22}$: −2.17° (C=1.07, CH$_2$Cl$_2$)
NMR(CDCl$_3$) δ: 0.86–0.91(6H,m), 1.29–1.61(18H,m), 2.28–2.42(1H,m), 2.61–2.76(3H,m), 3.52(2H,t,J=6.60 Hz), 3.61–3.75(2H,m), 3.92(1H,dd,J=9.16 Hz, 12.09 Hz), 4.62–4.67(1H,m), 7.24(2H,d,J=8.06 Hz), 7.35(2H,d,J=8.42 Hz), 7.48(2H,d,J=8.42 Hz), 7.57(2H,d,J=8.06 Hz)

(2R,4R) isomer:

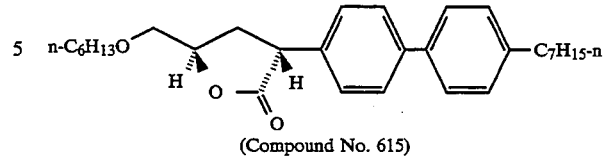

(Compound No. 615)

Phase transition temperature: C —48° C.→ I $[\alpha]_D^{22}$: −37.95° (C=1.003, CH$_2$Cl$_2$)
NMR(CDCl$_3$) δ: 0.86–0.90(6H,m), 1.29–1.60(18H,m), 2.45–2.57(1H,m), 2.61–2.74(3H,m), 3.51(2H,t,J=6.68 Hz), 3.60–3.75(2H,m), 4.09(1H,t,J=9.35 Hz), 4.74–4.78(1H,m), 7.24(2H,d,J=8.06 Hz), 7.33(2H,d,J=8.43 Hz), 7.48(2H,d,J=8.43 Hz), 7.57(2H,d,J=8.06 Hz)

TABLE 1

(II)-1

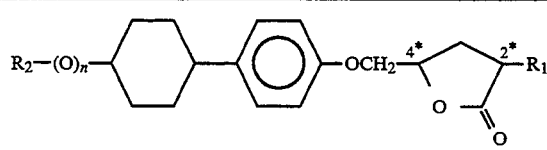

| Compound No. | R$_1$ | R$_2$ | n | 2* | 4* | mp (°C.) | $[\alpha]_D$ (CH$_2$Cl$_2$) |
|---|---|---|---|---|---|---|---|
| 101 | CH$_3$ | n-C$_3$H$_7$ | 0 | S | R | 139 | −27.82° (C = 1.03) |
| 102 | " | " | " | R | R | 117 | −16.82° (C = 0.98) |
| 103 | n-C$_9$H$_{19}$ | " | " | S | R | 127 | −23.48° (C = 1.027) |
| 104 | " | " | " | R | R | 113 | −31.45° (C = 1.432) |
| 105 | CH$_3$ | n-C$_5$H$_{11}$ | " | R | S | 101 | +20.25° (C = 0.490) |
| 106 | " | " | " | S | S | 101 | +14.03° (C = 0.493) |
| 107 | C$_2$H$_5$ | " | " | R | S | 99 | +21.24° (C = 0.423) |
| 108 | " | " | " | S | S | 98 | +29.57° (C = 0.165) |
| 109 | n-C$_4$H$_9$ | " | 0 | R | S | 85 | +20.37° (C = 1.05) |
| 110 | " | " | " | S | S | 84 | +33.45° (C = 0.658) |
| 111 | n-C$_7$H$_{15}$ | " | " | S | S | 110 | +27.61° (C = 0.039) |
| 112 | n-C$_{11}$H$_{23}$ | " | " | R | S | 122 | +19.65° (C = 1.053) |
| 113 | " | " | " | S | S | 105 | +21.64° (C = 1.085) |
| 114 | CH$_3$ | n-C$_9$H$_{19}$ | " | R | S | 102 | +20.00° (C = 0.888) |
| 115 | " | " | " | S | S | 85 | +16.60° (C = 1.03) |
| 116 | n-C$_3$H$_{11}$ | " | " | R | S | 117 | +19.57° (C = 1.17) |
| 117 | " | " | " | S | S | 98 | +27.52° (C = 1.194) |

TABLE 2

(II)-2

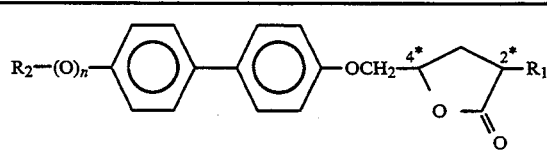

| Compound No. | R$_1$ | R$_2$ | n | 2* | 4* | mp (°C.) | $[\alpha]_D$ (CH$_2$Cl$_2$) |
|---|---|---|---|---|---|---|---|
| 201 | CH$_3$ | n-C$_6$H$_{13}$ | 0 | R | S | 129 | +27.58° (C = 1.076) |
| 202 | " | " | " | S | S | 125 | +19.20° (C = 1.08) |
| 203 | n-C$_6$H$_{13}$ | " | " | R | S | 136 | +27.36° (C = 0.876) |
| 204 | " | " | " | S | S | 140 | +37.78° (C = 1.048) |
| 205 | n-C$_{10}$H$_{21}$ | " | " | R | S | 132 | +25.56° (C = 1.037) |
| 206 | " | " | " | S | S | 136 | +35.00° (C = 1.273) |
| 207 | CH$_3$ | n-C$_8$H$_{17}$ | " | R | S | 129 | +25.24° (C = 1.048) |
| 208 | " | " | " | S | S | 127 | +17.53° (C = 1.039) |
| 209 | n-C$_3$H$_7$ | " | " | R | S | 117 | +22.50° (C = 0.504) |
| 210 | " | " | " | S | S | 115 | +32.67° (C = 1.081) |
| 211 | n-C$_9$H$_{19}$ | " | " | R | S | 132 | +22.26° (C = 0.826) |
| 212 | " | " | " | S | S | 134 | +33.29° (C = 1.076) |
| 213 | n-C$_{12}$H$_{25}$ | " | " | R | S | 130 | +24.52° (C = 1.870) |
| 214 | " | " | " | S | S | 133 | +31.20° (C = 1.010) |
| 215 | CH$_3$ | " | 1 | R | S | 133 | +21.33° (C = 0.553) |

TABLE 2-continued

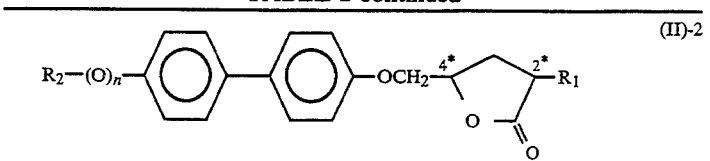
(II)-2

| Compound No. | R₁ | R₂ | n | 2* | 4* | mp (°C.) | $[\alpha]_D$ (CH₂Cl₂) |
|---|---|---|---|---|---|---|---|
| 216 | " | " | " | S | S | 119 | +22.35° (C = 0.470) |
| 217 | n-C₈H₁₇ | " | " | S | S | 139 | +28.59° (C = 0.674) |
| 218 | n-C₄H₉ | n-C₁₂H₂₅ | 0 | R | R | 130 | −28.56° (C = 1.06) |
| 219 | " | " | " | S | R | 128 | −22.98° (C = 1.07) |

TABLE 3

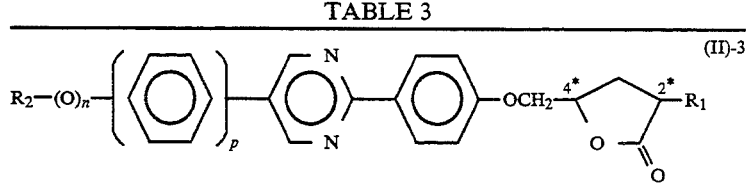
(II)-3

| Compound No. | R₁ | R₂ | n | p | 2* | 4* | mp (°C.) | $[\alpha]_D$ (CH₂Cl₂) |
|---|---|---|---|---|---|---|---|---|
| 301 | n-C₆H₁₃ | n-C₈H₁₇ | 0 | 0 | —ᵃ | S | 116 | +37.93° (C = 1.024) |
| 302 | CH₃ | " | 1 | " | R | S | 115 | |
| 303 | " | " | " | " | S | S | 154 | |
| 304 | n-C₄H₉ | " | " | " | R | S | 108 | +25.02° (C = 0.23) |
| 305 | " | " | " | " | S | S | 130 | +41.04° (C = 0.137) |
| 306 | n-C₇H₁₅ | " | " | " | R | S | 192 | |
| 307 | " | " | " | " | S | S | 135 | |
| 308 | n-C₁₀H₂₁ | " | " | " | R | S | 100 | |
| 309 | " | " | " | " | S | S | 127 | |
| 310 | n-C₉H₁₉ | n-C₁₀H₂₁ | 0 | " | R | S | 100 | |
| 311 | " | " | " | " | S | S | 139 | |
| 312 | n-C₁₂H₂₅ | " | " | " | R | S | 89 | +17.12° (C = 0.398) |
| 313 | " | " | " | " | S | S | 127 | +26.01° (C = 1.062) |
| 314 | n-C₅H₁₁ | n-C₈H₁₇ | 1 | 1 | R | S | b | |
| 315 | " | " | " | " | S | S | c | |
| 316 | n-C₈H₁₇ | " | " | " | R | S | d | +7.09° (C = 0.115) |
| 317 | " | " | " | " | S | S | e | +19.45° (C = 0.613) |
| 318 | n-C₁₁H₂₃ | " | " | " | R | S | f | +11.93° (C = 1.180) |
| 319 | " | " | " | " | S | S | g | +20.93° (C = 1.116) |

ᵃmixture of (2S, 4S)/(2R, 4S) = 9/1 b: $C \xrightarrow{138} SmX \xrightarrow{145} SmC^* \xrightarrow{201} N \xrightarrow{202} I$ (°C.)

c: $C \xrightarrow{150} SmX \xrightarrow{155} SmC^* \xrightarrow{190} I$ (°C.)

d: $C \xrightarrow{126} SmC^* \xrightarrow{199} I$ (°C.)

e: $C \xrightarrow{161} SmC^* \xrightarrow{186} I$ (°C.)

f: $C \xrightarrow{120} SmX \xrightarrow{133} SmC^* \xrightarrow{195} I$ (°C.)

g: $C \xrightarrow{150} SmX \xrightarrow{155} SmC^* \xrightarrow{183} I$ (°C.)

TABLE 4

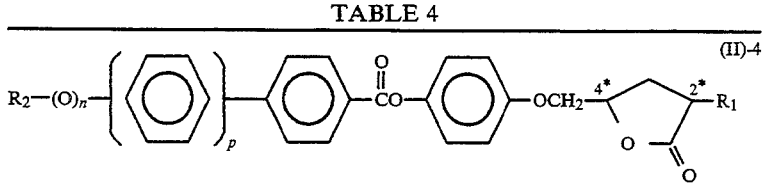
(II)-4

| Compound No. | R₁ | R₂ | n | p | 2* | 4* | mp (°C.) | $[\alpha]_D$ (CH₂Cl₂) |
|---|---|---|---|---|---|---|---|---|
| 401 | n-C₄H₉ | n-C₈H₁₇ | 1 | 0 | S | S | 91 | +30.07° (C = 1.038) |
| 402 | " | " | " | " | R | S | 93 | +20.00° (C = 0.803) |
| 403 | " | n-C₇H₁₅ | 1 | 1 | S | S | a | +28.77° (C = 1.017) | a: $C \xrightarrow{141} SmC^* \xrightarrow{147} SmA \xrightarrow{184} I$ (°C.)

TABLE 5

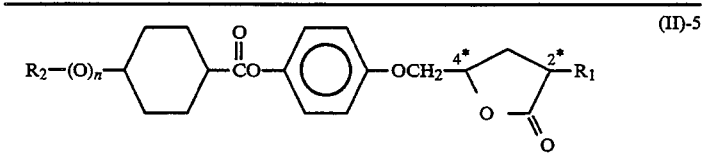

(II)-5

| Compound No. | $R_1$ | $R_2$ | n | 2* | 4* | mp (°C.) | $[\alpha]_D$ ($CH_2Cl_2$) |
|---|---|---|---|---|---|---|---|
| 411 | n-$C_4H_9$ | n-$C_5H_{11}$ | 1 | S | S | 85 | +31.89° (C = 1.043) |

TABLE 6

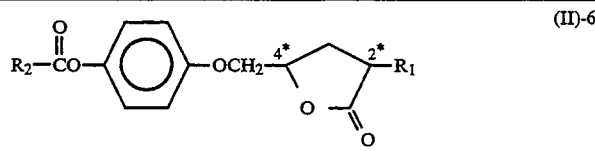

(II)-6

| Compound No. | $R_1$ | $R_2$ | 2* | 4* | mp (°C.) | $[\alpha]_D$ ($CH_2Cl_2$) |
|---|---|---|---|---|---|---|
| 421 | n-$C_4H_9$ | n-$C_5H_{11}$ | S | S | 72 | +39.67° (C = 1.060) |

TABLE 7

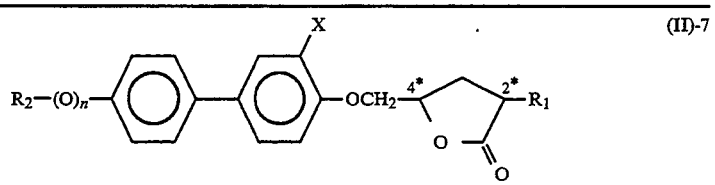

(II)-7

| Compound No. | $R_1$ | $R_2$ | n | X | 2* | 4* | mp (°C.) | $[\alpha]_D$ ($CH_2Cl_2$) |
|---|---|---|---|---|---|---|---|---|
| 501 | n-$C_3H_7$ | n-$C_8H_{17}$ | 0 | —CN | R | S | 80 | +18.26° (C = 0.87) |
| 502 | " | " | " | " | S | S | 86 | +31.83° (C = 1.09) |
| 503 | " | " | " | F | R | S | 83 | +24.76° (C = 1.02) |
| 504 | " | " | " | " | S | S | 92 | +38.17° (C = 1.00) |
| 505 | $CH_3$ | " | " | " | R | S | 89 | +27.00° (C = 1.02) |
| 506 | " | " | " | " | S | S | 95 | +21.06° (C = 1.01) |
| 507 | n-$C_3H_7$ | " | 1 | " | R | S | 100 | +21.51° (C = 0.79) |
| 508 | " | " | " | " | S | S | 125 | +38.35° (C = 1.02) |

TABLE 8

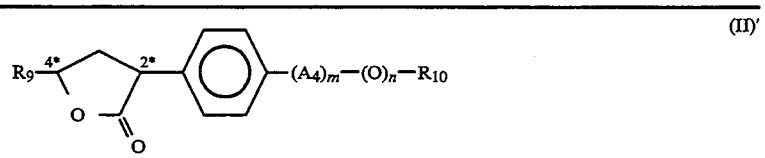

(II)'

| Compound No. | $R_9$ | $R_{10}$ | $A_4$ | m | n | 2* | 4* | mp (°C.) | $[\alpha]_D$ ($CH_2Cl_2$) |
|---|---|---|---|---|---|---|---|---|---|
| 601 | allyl-OCH$_2$— | n-$C_4H_9$ | cyclohexyl | 1 | 0 | S | R | 107 | −3.22° (C = 1.033) |
| 602 | " | " | " | " | " | R | R | 76 | −40.42° (C = 1.024) |
| 603 | n-$C_{11}H_{21}$ | " | cyclohexyl | 1 | 0 | R | R | 116 | −3.57° (C = 1.035) |
| 604 | " | " | " | " | " | S | R | a | +31.02° (C = 1.038) |

TABLE 8-continued $$R_9 \overset{4^*}{-} \underset{O}{\overset{O}{\diagdown}} \overset{2^*}{-} \langle \text{Ph} \rangle - (A_4)_m - (O)_n - R_{10} \quad (II)'$$

| Compound No. | $R_9$ | $R_{10}$ | $A_4$ | m | n | 2* | 4* | mp (°C.) | $[\alpha]_D$ (CH$_2$Cl$_2$) |
|---|---|---|---|---|---|---|---|---|---|
| 605 | CH$_3$OCH$_2$— | n-C$_7$H$_{15}$ | —⟨Ph⟩— | 1 | " | R | S | 68 | +0.35° (C = 1.01) |
| 606 | " | " | " | " | " | S | S | 66 | +34.16° (C = 1.013) |
| 607 | n-C$_5$H$_{11}$ | " | " | " | " | R | R | 102 | −5.66° (C = 1.089) |
| 608 | " | " | " | " | " | S | R | 99 | +33.48° (C = 1.027) |
| 609 | n-C$_7$H$_{15}$ | n-C$_8$H$_{12}$ | — | 0 | 1 | R | R | 75 | −3.72° (C = 1.018) |
| 610 | " | " | " | " | " | S | R | 48 | +34.23° (C = 1.00) |
| 611 | n-C$_6$H$_{13}$OCH$_2$— | n-C$_9$H$_{19}$ | —⟨Ph⟩— | 1 | " | R | S | 92 | +1.36° (C = 1.06) |
| 612 | " | " | " | " | " | S | S | 64 | +29.27° (C = 1.16) |
| 613 | n-C$_7$H$_{15}$ | " | " | " | " | R | R | 126 | −5.42° (C = 1.66) |
| 614 | " | " | " | " | " | S | R | b | +29.33° (C = 0.95) |
| 615 | n-C$_6$H$_{11}$OCH$_2$— | n-C$_7$H$_{15}$ | —⟨Ph⟩— | " | 0 | R | R | 48 | −37.95° (C = 1.003) |
| 616 | " | " | " | " | " | S | R | 71 | −2.17° (C = 1.070) | a: C$\overset{71}{-}$SmX$\overset{113}{-}$I (°C.)

b: C$\overset{96}{-}$SmC*$\overset{114}{-}$SmA$\overset{118}{-}$I (°C.)

EXAMPLE 1

A nematic liquid crystal composition (1) shown in Table 9 was prepared. A Cano type cell in the shape of wedge was made by conducting a horizontal orientation treatment of a pair of glass substrates and facing their orientation layers in the manner that their rubbed directions are reverse.

The thickness of each of the parts of the cell was measured. Each of the compounds shown in Table 10 in an amount of about 1% by weight was added to the liquid crystal composition (1) obtain a nematic liquid crystal compositions, which was injected to the above Cano type cell. This cell was placed at the position between 2 sheets of polarizing plates arranged in perpendicular with respect to their polarizing directions and the disclination line was observed. The helical pitch of the injected nematic liquid crystal composition was determined on the basis of the thickness of the cell at the position where a disclination line appeared. The 1/pi of each of the compounds was evaluated from the helical pitch value, using the equation (X). The results are shown in Table 10.

TABLE 9

Nematic Liquid Crystal Composition (1)

| Compound No. | N $\xrightarrow{60° C.}$ I | |
|---|---|---|
| 801 | C$_6$H$_{13}$—⟨pyrimidine⟩—⟨Ph⟩—OC$_6$H$_{13}$ | 34.9% |
| 802 | C$_6$H$_{13}$—⟨pyrimidine⟩—⟨Ph⟩—OC$_7$H$_{15}$ | 20.1% |
| 803 | C$_6$H$_{13}$—⟨pyrimidine⟩—⟨Ph⟩—OC$_9$H$_{19}$ | 30.0% |
| 804 | C$_6$H$_{13}$—⟨pyrimidine⟩—⟨Ph⟩—OC$_{11}$H$_{23}$ | 15.0% |

TABLE 10

| Compound No. | Structure | Pitch in nematic phase Direction | 1/Pi | Direction of Ps |
|---|---|---|---|---|
| 110 | (2S, 4S)C$_5$H$_{11}$—[cyclohexyl]—[phenyl]—OCH$_2$*—CH—CH$_2$—*CH—C$_4$H$_9$ (lactone ring) | L | −4.13 | — |
| 202 | (2S, 4S)C$_6$H$_{13}$—[phenyl]—[phenyl]—OCH$_2$*—CH—CH$_2$—*CH—CH$_3$ (lactone ring) | L | −9.25 | — |
| 204 | (2S, 4S)C$_6$H$_{13}$—[phenyl]—[phenyl]—OCH$_2$*—CH—CH$_2$—*CH—C$_6$H$_{13}$ (lactone ring) | L | −3.26 | — |
| 208 | (2S, 4S)C$_8$H$_{17}$—[phenyl]—[phenyl]—OCH$_2$*—CH—CH$_2$—*CH—CH$_3$ (lactone ring) | L | −8.14 | — |
| 210 | (2S, 4S)C$_8$H$_{17}$—[phenyl]—[phenyl]—OCH$_2$*—CH—CH$_2$—*CH—C$_3$H$_7$ (lactone ring) | L | −4.72 | — |
| 301 | (2S, 4S)C$_8$H$_{17}$—[phenyl]—[phenyl]—OCH$_2$*—CH—CH$_2$—*CH—C$_6$H$_{13}$ (lactone ring) | L | −4.90 | — |
| 704 | (R)C$_6$H$_{13}$O—[phenyl]—COO—[phenyl]—COO*CHC$_6$H$_{13}$ / CH$_3$ | R | +10.5 | — |
| 705 | (S)C$_7$H$_{15}$O—[phenyl]—COO—[phenyl]—[phenyl]—O*CHC$_6$H$_{13}$ / CH$_3$ | R | +1.96 | — |
| 701 | (S)C$_8$H$_{17}$O—[pyrazine]—[phenyl]—OCH$_2$CH$_2$*CHC$_2$H$_5$ / CH$_3$ | R | +1.07 | — |
| 702 | (S)C$_{11}$H$_{23}$O—[pyrazine]—[phenyl]—OCH$_2$CH$_2$*CHC$_2$H$_5$ / CH$_3$ | R | +0.89 | — |
| 703 | (S)C$_8$H$_{17}$O—[phenyl]—[pyridine]—[phenyl]—OCH$_2$*CHC$_2$H$_5$ / CH$_3$ | L | −0.21 | + |

TABLE 10-continued

| Compound No. | Structure | Pitch in nematic phase Direction | 1/Pi | Direction of Ps |
|---|---|---|---|---|
| 206 | 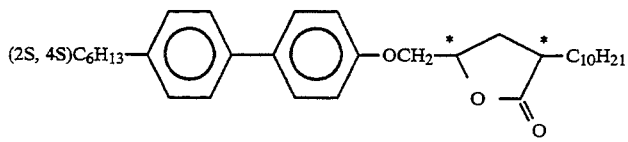 | L | −1.14 | — |
| 508 | 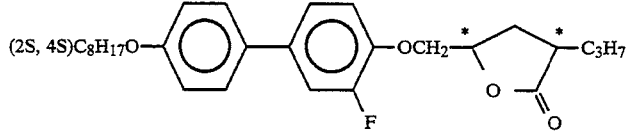 | R | +5.94 | — |
| 507 | 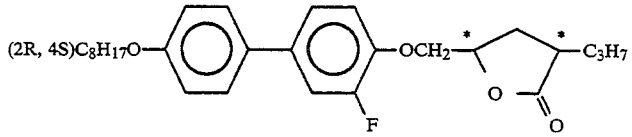 | L | −4.64 | — |
| 502 | 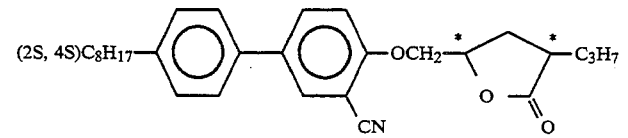 | L | −0.86 | — |
| 501 | 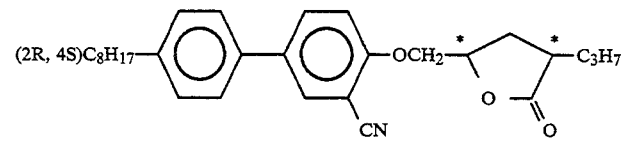 | L | −13.7 | — |
| 616 | 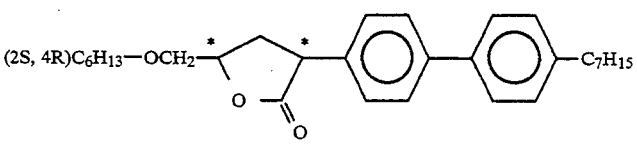 | R | +9.31 | — |
| 615 | 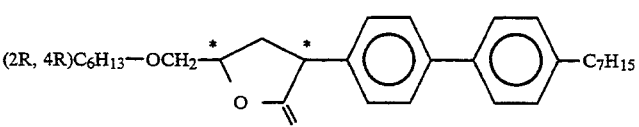 | R | +4.64 | — |
| 708 | 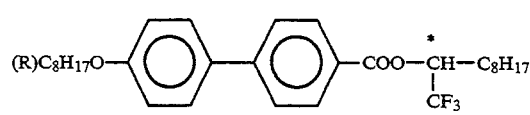 | L | −3.25 | — |

EXAMPLE 2

Each of the compounds shown in Table 11 in an amount of 30% by weight was added to the liquid crystal composition (1) to obtain a liquid crystal composition showing nematic phase. The helical pitch directions in nematic phase of the compounds in Table 11 are well known. On the other hand, each of the compounds shown in Table 10 in an amount of 1 to 30% by weight was also added to the liquid crystal composition (1) to obtain compositions showing nematic phase. A nematic liquid crystal composition prepared from a compound in Table 11 was brought in contact on a slide with that prepared from a compound in Table 10 and an area where both the compositions are in contact was observed by a polarization microscope. The direction of the helical pitch induced in a compound in Table 10 in nematic phase was determined by observing whether a schlieren structure appears or not, which occurs in the contacting area only when the helical pitch is very large.

TABLE 11

| Compound No. | Structure | Direction of pitch in nematic phase |
|---|---|---|
| 706 | (S)C$_8$H$_{17}$O—⟨◯⟩—COO—⟨◯⟩—⟨◯⟩—OCHC$_6$H$_{13}$ (*) / CH$_3$ | R |
| 707 | (S)C$_6$H$_{13}$O—⟨◯⟩—COO—⟨◯⟩—COOCHC$_6$H$_{13}$ (*) / CH$_3$ | L |

EXAMPLE 3

The liquid crystal composition (2) shown in Table 12 was prepared, which is a nonchiral smectic C liquid crystal composition containing no optically active compound. Each of the compounds shown in Table 10 in an amount of 2% by weight was added to the liquid crystal composition (2) to obtain a chiral smectic C liquid crystal composition.

Two glass substrates each was laminated by ITO film electrode, SiO$_2$ insulating film and PVA film. The upper PVA film was rubbed. These two glass substrates were set to make a cell leaving 2 μm clearance between these substrates. The above chiral smectic C liquid crystal composition was injected to the above cell. This cell was placed at the position between 2 sheets of polarizers arranged in perpendicular with respect to their polarizing directions. When voltage was applied to the cell, a change was observed in the intensity of the transmitted light. The direction of the spontaneous polarization (Ps) induced in smectic C phase of each of the compounds was determined from the relationship of the direction of the applied voltage with the response direction of liquid crystal molecules found on the basis of the change of the intensity of the transmitted light. The results are shown in Table 12.

TABLE 12

Nonchiral smectic C liquid crystal composition (2)

Compound No. | $S_C \xrightarrow{51° C.} S_A \xrightarrow{64° C.} N \xrightarrow{70° C.} I$

| 805 | C$_7$H$_{15}$—⟨pyrimidine(N,N)⟩—⟨◯⟩—OC$_7$H$_{15}$ | 10% |
| 806 | C$_7$H$_{15}$—⟨pyrimidine(N,N)⟩—⟨◯⟩—OC$_8$H$_{17}$ | 5% |
| 807 | C$_7$H$_{15}$—⟨pyrimidine(N,N)⟩—⟨◯⟩—OC$_9$H$_{19}$ | 15% |
| 809 | C$_8$H$_{17}$—⟨pyrimidine(N,N)⟩—⟨◯⟩—OC$_8$H$_{17}$ | 20% |

TABLE 12-continued

Nonchiral smectic C liquid crystal composition (2)

Compound No. | $S_C \xrightarrow{51° C.} S_A \xrightarrow{64° C.} N \xrightarrow{70° C.} I$

| 811 | C$_8$H$_{17}$—⟨pyrimidine(N,N)⟩—⟨◯⟩—OC$_{10}$H$_{21}$ | 32% |
| 812 | C$_9$H$_{19}$—⟨pyrimidine(N,N)⟩—⟨◯⟩—OC$_6$H$_{13}$ | 18% |

EXAMPLE 4

Ferroelectric liquid crystal compositions 30 to 35 were prepared from the compounds shown in Tables 10 and 13. These compositions were prepared so as to have a phase sequence of a smectic C phase, smectic A phase and nematic phase, and 20 μm of a helical pitch in nematic phase. The values of the phase change temperature and the helical pitch in nematic phase obtained by calculating using the equation (X) are shown in Table 15.

A Cano type cell in the shape of wedge similar to that used in Example 1 was prepared except that the thickness in the thicker portion of the cell is 10 μm. Each of the compositions 30 to 35 was injected to the above cell. No disclination line was observed in the above cells, which demonstrated that the helical pitches in nematic phase of these compositions are 20 μm or more.

EXAMPLE 5

Two glass substrates each was laminated by ITO film electrode, SiO$_2$ insulating film and PVA film. The upper PVA film was rubbed. These two glass substrates were set to make a cell facing their orientation films each to others in the same rubbing direction and leaving 2 μm clearance between these films. Each of the ferroelectric liquid crystal compositions prepared in Example 4 was injected to the above cell. The cell was then heated at a temperature to change the liquid crystal composition into an isotropic liquid and then cooled to room temperature at the rate of 1° C./min to obtain a ferroelectric liquid crystal element having good orientation.

The above element was placed at the position between two sheets of polarizers arranged in perpendicular with respect to their polarizing directions. A voltage was applied to the cell and the characteristics were evaluated.

TABLE 13
| Compound No. | Structure |
|---|---|
| 805 | 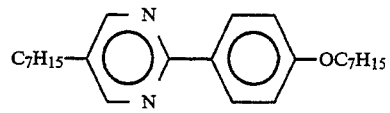 |
| 806 | 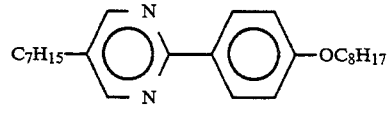 |
| 807 | 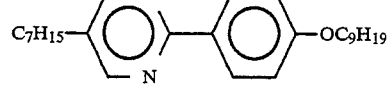 |
| 808 | 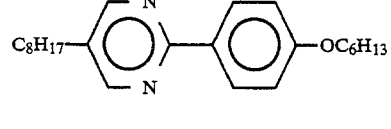 |
| 809 | 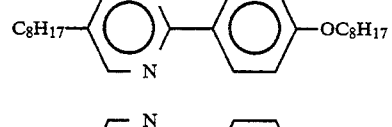 |
| 810 | 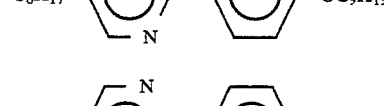 |
| 811 | 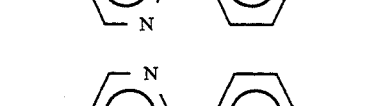 |
| 812 | 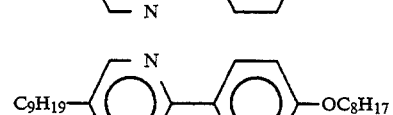 |
| 813 | 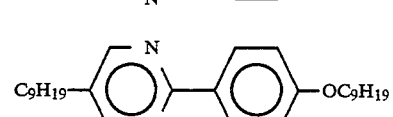 |
| 814 | 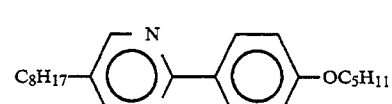 |
| 815 | 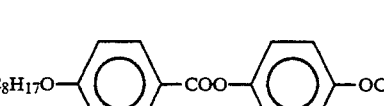 |
| 903 | 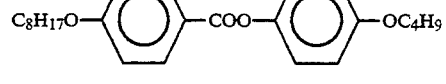 |
| 904 | 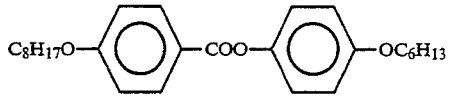 |

TABLE 13-continued

| Compound No. | Structure |
|---|---|
| 906 | 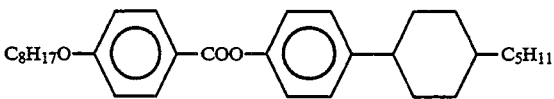 $C_8H_{17}O$—⬡—COO—⬡—⬡—$C_5H_{11}$ |
| 907 | $C_{10}H_{21}O$—⬡—COO—⬡—⬡—$C_5H_{11}$ |
| 909 | $C_8H_{17}$—⬡—⬡—COO—$CH_2CH_2$—$C_6F_{13}$ |
| 901 | $C_6H_{13}$—⬡—COO—⬡—$C_8H_{17}$ |
| 902 | $C_9H_{19}$—⬡—COO—⬡—$OC_8H_{17}$ |
| 905 | $C_8H_{17}O$—⬡—COO—⬡—$OC_8H_{17}$ |
| 908 | $C_9H_{19}$—⬡—COO—⬡—⬡—$OC_8H_{17}$ |

TABLE 14

| Compound No. | Composition No. 30 | Composition No. 31 | Composition No. 32 | Composition No. 33 | Composition No. 34 | Composition No. 35 |
|---|---|---|---|---|---|---|
| 110 |  | 2.2 | 3.4 | 1.4 | 1.4 | 2.5 |
| 202 | 0.4 |  |  |  |  |  |
| 204 | 0.4 | 1.0 | 1.2 |  |  | 0.8 |
| 208 | 0.4 |  |  |  |  |  |
| 210 | 0.4 | 0.5 | 0.6 | 0.8 | 0.8 |  |
| 301 |  |  |  |  |  | 1.8 |
| 704 |  |  |  |  |  | 1.6 |
| 705 |  | 5.5 | 5.3 | 3.0 | 3.0 | 2.2 |
| 701 |  | 3.9 | 10.0 | 3.0 | 3.0 | 1.7 |
| 702 | 11.8 |  |  |  |  |  |
| 703 |  |  |  |  |  | 3.2 |
| 805 | 3.5 | 4.3 | 3.5 | 4.6 | 4.6 |  |
| 806 | 23.0 | 8.7 | 7.0 | 9.2 | 9.2 |  |
| 807 | 10.6 | 13.0 | 10.5 | 13.8 | 13.8 | 7.1 |
| 808 |  |  |  |  |  | 3.5 |
| 809 | 14.1 | 17.4 | 14.0 | 18.4 | 18.3 | 14.1 |
| 810 |  |  |  |  |  | 3.5 |
| 811 | 21.3 | 26.1 | 21.0 | 27.4 | 27.3 | 14.2 |
| 812 | 14.1 | 17.4 | 14.0 | 18.4 | 18.4 | 3.5 |
| 813 |  |  |  |  |  | 10.6 |
| 814 |  |  |  |  |  | 14.1 |
| 815 |  |  |  |  |  | 2.8 |
| 903 |  |  |  |  |  | 3.5 |
| 904 |  |  |  |  |  | 4.7 |
| 906 |  |  | 4.7 |  |  | 2.3 |
| 907 |  |  | 4.6 |  |  | 2.3 |
| 909 |  |  | 0.2 |  | 0.2 |  |

| Compound No. | Composition No. 49 | Composition No. 50 | Composition No. 51 | Composition No. 53 | Composition No. 54 | Composition No. 55 | Composition No. 58 |
|---|---|---|---|---|---|---|---|
| 110 | 1.8 |  |  |  |  |  |  |
| 208 |  |  |  |  | 2.0 |  | 2.0 |
| 210 |  |  |  |  |  | 2.0 |  |

TABLE 14-continued

| | | | | | | | |
|---|---|---|---|---|---|---|---|
| 301 | | | | | | | |
| 704 | 1.7 | | | | | | |
| 705 | 1.1 | | | | | | |
| 701 | | | | | 3.9 | 2.8 | |
| 805 | | | | 5.0 | 4.6 | 4.7 | 4.8 |
| 806 | | | | 8.8 | 9.2 | 9.3 | 9.6 |
| 807 | 6.6 | 5.9 | 7.1 | 14.7 | 13.9 | 14.0 | 14.4 |
| 808 | 2.9 | 2.6 | 3.1 | | | | |
| 809 | 10.2 | 9.2 | 11.1 | 13.6 | 18.5 | 18.6 | 19.2 |
| 811 | 14.0 | 12.5 | 14.9 | 33.3 | 27.7 | 27.9 | 28.9 |
| 812 | 6.6 | 5.9 | 7.1 | 17.6 | 18.5 | 18.6 | 19.2 |
| 813 | 13.0 | 11.5 | 14.0 | | | | |
| 814 | 13.0 | 11.5 | 14.0 | | | | |
| 815 | 6.6 | 5.9 | 7.1 | | | | |
| 906 | 3.6 | 5.3 | 3.0 | | | | |
| 907 | 3.6 | 5.3 | 3.0 | | | | |
| 909 | | | | | 0.3 | 0.3 | |
| 508 | 0.5 | | 2.3 | | | | |
| 507 | | | 2.9 | | | | |
| 502 | 1.0 | | | 2.0 | | | |
| 501 | 1.2 | | | | | | |
| 708 | | 4.5 | | | | | |
| 901 | 2.7 | 3.8 | 2.2 | | | | |
| 912 | 3.6 | 5.3 | 3.0 | | | | |
| 905 | 3.6 | 5.3 | 3.0 | | | | |
| 908 | 2.7 | 3.8 | 2.2 | | | | |

TABLE 15

| Composition No. | Phase transition (°C.) | | | | Calculated value of pitch in nematic phase (µm) | Response time (µsec) | Tilt angle θ (deg) |
|---|---|---|---|---|---|---|---|
| | $S_C$ | $S_A$ | N | I | | | |
| 30 | .51 | .67 | .69 | . | +280 | 127 | 16 |
| 31 | .47 | .62 | .67 | . | +400 | 59 | 19 |
| 32 | .46 | .63 | .72 | . | +330 | 66 | 19 |
| 33 | .49 | .63 | .68 | . | −180 | 89 | 18 |
| 34 | .49 | .64 | .68 | . | −180 | 65 | 18 |
| 35 | .44 | .71 | .76 | . | +170 | 136 | 18 |

| Composition No. | Phase transition (°C.) | | | | Calculated value of pitch in nematic phase (µm) | Response time (µsec) | Tilt angle θ (deg) | Memory angle 2θ (deg) |
|---|---|---|---|---|---|---|---|---|
| | $S_C$ | $S_A$ | N | I | | | | |
| 49 | .40 | .72 | .77 | . | −57 | 57 | | 9 |
| 50 | .46 | .73 | .79 | . | +83 | 107 | 14 | 13 |
| 51 | .57 | .75 | .79 | . | +490 | 49 | 21 | 13 |
| 53 | .47 | .61 | .67 | . | −58 | 128 | 19 | 11 |
| 54 | .49 | .64 | .67 | . | +54 | 72 | 20 | 15 |
| 55 | .49 | .63 | .67 | . | +52 | 92 | 21 | 11 |
| 58 | .49 | .60 | .66 | . | −120 | 69 | 22 | 9 |

What is claimed is:

1. A ferroelectric liquid crystal device having a pair of substrates each provided with voltage application means, an orientation control layer formed on at least one of the substrates, and a layer of ferroelectric liquid crystal composition formed between the pair of substrates, the device being characterized in that the ferroelectric liquid crystal composition comprises at least one compound (a) having an optically active group of the formula (I):

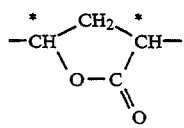

and at least one compound (b) which is reverse to the compound (a) in the direction of a helical pitch induced in a nematic phase, the liquid crystal composition exhibiting at least a smectic C phase, smectic A phase and nematic phase at least 20 µm in helical pitch, wherein the compound (a) is an optically active compound of the formula (II):

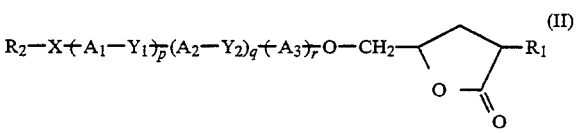

wherein $A_1$, $A_2$ and $A_3$ are each a 6-membered ring containing group selected from the group consisting of benzene, pyridine, pyrimidine, pyrazine, pyridazine, piperazine, cyclohexane, dioxacyclohexane, bicyclo octane and naphthalene ring, wherein one or more hydrogen atoms in the 6-membered ring-containing group may be substituted with a fluorine, chlorine or bromine atom, or cyano, nitro, methyl or methoxy group, X is —O—, —COO—, —OCO— or a single bond, $Y_1$ and $Y_2$ are each —COO—, —OCO—, —OCH$_2$—, —CH$_2$O—, —CH$_2$CH$_2$—, —CH=CH—, —C≡C— or a single bond, $R_1$ and $R_2$ are a straight-chain or branched-chain alkyl having 1 to 15 carbon atoms, and n, p, q and r are each an integer of 0 to 1, and provided that formula II is not:

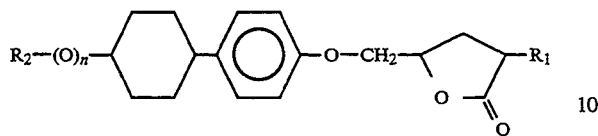

and,
wherein the compound (b) is a compound:
(i) represented by formula (II) as defined above; or
(ii) represented by one of the formulae:

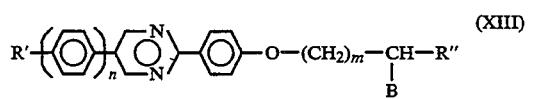 (XIII)

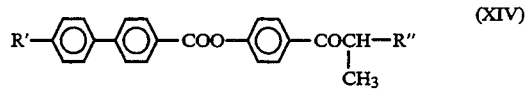 (XIV)

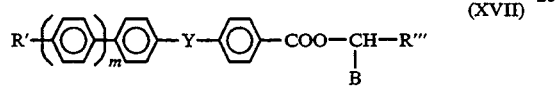 (XVII)

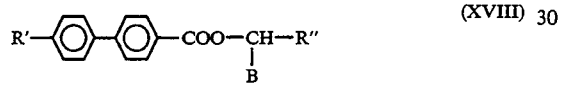 (XVIII)

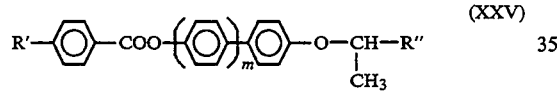 (XXV)

or

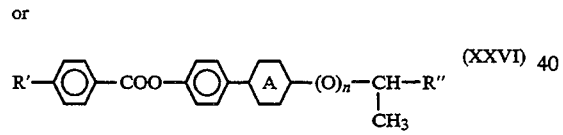 (XXVI)

wherein R' and R" are the same or different and are each a straight-chain or branched-chain $C_{1-15}$ alkyl alkoxy group, R''' is straight-chain or branched-chain $C_{1-15}$ alkyl or alkoxy group or $CH_2COOC_2H_5$, B is $CH_3$, CN, $CF_3$, $CHF_2''$, $CH_2F$ or a halogen (Cl, F or Br), Y is —COO—, —OCO—, —OCH$_2$—, —CH$_2$O—,

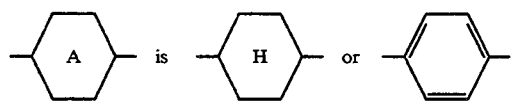

and n and m are each 0 or 1.

2. A device as defined in claim 1 wherein the group $R_2$—X—($A_1$—$Y_1$)$_p$—$A_2Y_2$)$_q$—($A_3$)$_r$— of the optically active compound of the formula (II) is represented by one formula selected from among the formulae:

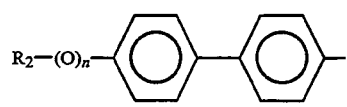

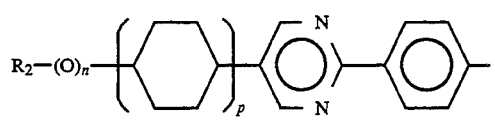

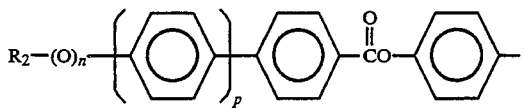

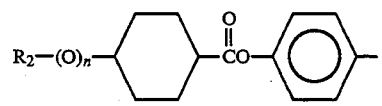

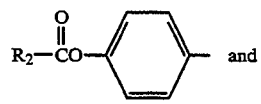

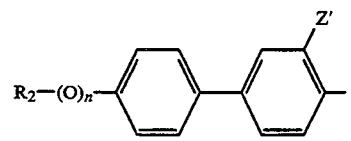 and

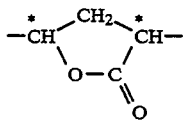

wherein $R_2$ and p are as defined for the formula (II), n is 0 or 1, and Z' is —CN or F.

3. A device as defined in claim 1 or 2 wherein in the formula (II), $R_1$ is a straight-chain or branched-chain $C_{1-12}$ alkyl and $R_2$ is a straight-chain or branched-chain $C_{5-11}$ alkyl.

4. A ferroelectric liquid crystal device having a pair of substrates each provided with voltage application means, an orientation control layer formed on at least one of the substrates, and a layer of ferroelectric liquid crystal composition formed between the pair of substrates, the device being characterized in that the ferroelectric liquid crystal composition comprises at least one compound (a) having and optically active group of the formula (I):

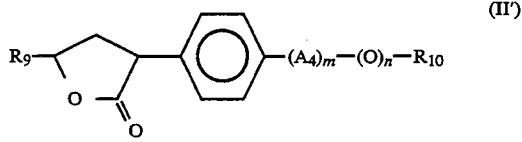 (I)

and at least one compound (b) which is reverse to the compound (a) in the direction of a helical pitch induced in a nematic phase, the liquid crystal composition exhibiting at least a smectic C phase, smectic A phase and nematic phase at least 20 μm in helical pitch,
wherein the compound (a) is an optically active compound of the formula (II'):

(II')

wherein $R_9$ is a straight-chain or branched-chain $C_{1-15}$ aliphatic hydrocarbon group having or not having an intervening oxygen atom, $R_{10}$ is a straight-chain or branched-chain $C_{1-15}$ alkyl group, A₄ is a phenylene group or cyclohexane group, and m and n are each 0 or 1, wherein R' and R" are the same of different and are each a straight-chain or branched-chain $C_{1-15}$ alkyl alkoxy group, R'" is straight-chain or branched-chain $C_{1-15}$ alkyl or alkoxy group or $CH_2COOC_2H_5$, B is $CH_3$, CN, $CF_3$, $CHF_{2''}$, $CH_2F$ or a halogen (Cl, F or Br), Y is —COO—, —OCO—, —OCH₂—, —CH₂O—, and n and m are each 0 or 1 and, wherein the compound (b) is a compound:
(i) represented by formula (II') as defined above; or
(ii) represented by one of the formulae:

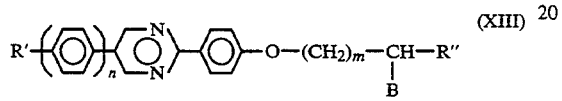   (XIII)

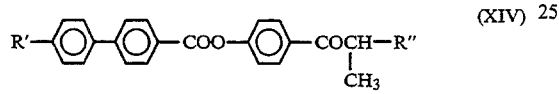   (XIV)

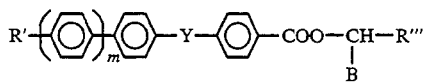   (XVII)

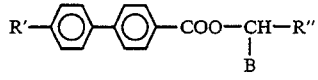   (XVIII)

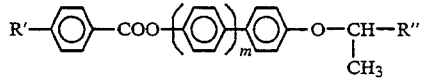   (XXV)

or

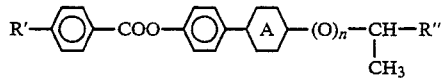   (XXVI)

wherein R' and R" are the same of different and are each a straight-chain or branched-chain $C_{1-15}$ alkyl alkoxy group, R'" is straight-chain or branched-chain $C_{1-15}$ alkyl or alkoxy group or $CH_2COOC_2H_5$, B is $CH_3$, CN, $CF_3$, $CHF_{2''}$, $CH_2F$ or a halogen (Cl, F or Br), Y is —COO—, —OCO—, —OCH₂, —CH₂O—, and n and m are each 0 or 1.

* * * * *